United States Patent [19]

Degen et al.

[11] Patent Number: 5,841,523

[45] Date of Patent: Nov. 24, 1998

[54] METHOD FOR PERFORMING SPECTROSCOPIC ANALYSIS OF INHOMOGENEOUS TEST SAMPLES

[75] Inventors: Beat R. Degen, Bellingham; Michael F. Garyantes, Medfield, both of Mass.

[73] Assignee: Chiron Diagnostics Corporation, E. Walpole, Mass.

[21] Appl. No.: 425,559

[22] Filed: Apr. 20, 1995

[51] Int. Cl.$^6$ .......................... G01N 33/48; G01N 21/00; G01J 3/00

[52] U.S. Cl. .................. 356/72; 356/73; 356/39; 356/300; 356/319; 356/326; 364/498; 364/570; 364/574; 364/578

[58] Field of Search ...................... 356/300–334, 356/73, 39–40, 72; 364/571.01, 571.04, 498, 570, 574, 578

[56] References Cited

U.S. PATENT DOCUMENTS

| | | | |
|---|---|---|---|
| 3,966,323 | 6/1976 | Matsuoka et al. | 356/96 |
| 4,627,014 | 12/1986 | Lo et al. | 356/300 |
| 4,885,711 | 12/1989 | Neff | 364/574 |
| 5,036,857 | 8/1991 | Semmlow et al. | 128/715 |
| 5,121,337 | 6/1992 | Brown | 364/571.04 |
| 5,226,417 | 7/1993 | Swedlow et al. | 128/633 |
| 5,291,426 | 3/1994 | Collins et al. | 364/571.04 |
| 5,379,238 | 1/1995 | Stark | 356/39 |
| 5,396,440 | 3/1995 | Coburn | 356/346 |
| 5,428,558 | 6/1995 | Cahill et al. | 356/307 |
| 5,568,400 | 10/1996 | Stark et al. | 364/498 |

FOREIGN PATENT DOCUMENTS 0479569  4/1992  European Pat. Off. .

*Primary Examiner*—Frank G. Font
*Assistant Examiner*—Jason D. Vierra-Eisenberg
*Attorney, Agent, or Firm*—Arthur S. Morgenstern; Charles L. Gagnebin, III; Robert P. Blackburn

[57] ABSTRACT

A method is provided for more accurately calculating the concentration of analytes or components in test samples. The method includes the use of an algorithm for analysis, and selection of sets of signal measurements from a spectrophotometer. Sets of signal measurements are selected to avoid inhomogeneities, i.e. air bubbles, artifacts and dilution, in test samples being analyzed. The method has application to the spectroscopic determination of the concentration of hemoglobin derivatives or fractions in a blood sample.

28 Claims, 35 Drawing Sheets

| |
|---|
| 1) Find leading edge ("x" number of consecutive data points passing threshold criterion) |
| 2) Collect all data windows with variability below "Threshold 1" |
| 3) Select data from one (or more) data windows satisfying #2 and a signal level criterion (lowest or highest) |
| 4) If no windows satisfy #2, collect all data windows with variability below "Threshold 2" |
| 5) Select data from one (or more) data windows satisfying #4 and a signal level criterion (lowest or highest signal) |
| 6) If no windows satisfy #4, select data from one or more lowest variability windows |
| 7) If selected variability(s) are greater than Threshold 3 post an error |

| | |
|---|---|
| 1) | Find leading edge ("x" number of consecutive data points passing threshold criterion) |
| 2) | Collect all data windows with variability below "Threshold 1" |
| 3) | Select data from one (or more) data windows satisfying #2 and a signal level criterion (lowest or highest) |
| 4) | If no windows satisfy #2, collect all data windows with variability below "Threshold 2" |
| 5) | Select data from one (or more) data windows satisfying #4 and a signal level criterion (lowest or highest signal) |
| 6) | If no windows satisfy #4, select data from one or more lowest variability windows |
| 7) | If selected variability(s) are greater than Threshold 3 post an error |

*FIG. 1*

```
/***********************************************
 *<N
 *>N
 *  FUNCTION: READ_PROCESS_DATA
 *
 *
 *
 *  Returns: SUCCESS | FAILURE
 *>D                                            | PSEUDO CODE |
 ***********************************************
```

*FIG. 22A*

```
*>P***************************************| CALLING SEQUENCE |****************************************/
static int read_process_data( int lead_edge, U_LONG *data)
/* lead_edge - Find The Leading Edge Of The Sample Or Not.       */
/* data      - Pointer To The Data That Contains The Final Information.   */
/*>E*/
{
    short     i, j, j_scan, jmax, lowest_vr_index;
    short     leading_edge_overlap, scan_index, edge_scan_index;
    short     consec_edge_cnt;
    D_LONG    start_tick, total_time;
    short     *region_index, index_index;

long edge_data = 0;
    D_LONG t_sum;
    long vr = 0;
    long sum, lowest_sum, highest_sum, lowest_vr;      /* The Current Variability. */
    struct HEATER_DATA heater_data;
    int    cover_status, status;
    D_LONG *data_start;
#ifdef DEBUG
    short out_count;
endif consec_edge_cnt = 0;
    scan_index = 0;

for (i = 0; i < NUM_TIME_TICKS; i++)
        temp_cover_status[ i] = 0;
```

*FIG. 22B*

```
if( lead_edge == FIND_LEAD_EDGE)
{
#ifdef DEBUG
    printf("*\r\nEdge Det %d\r\n", lead_edge_thresh);
#endif
/*****************************************************************/
/* Must Sum Up The Initial NUM_SAMPLE_SCANS Number Of Readings: */
/*****************************************************************/
for( i = 0; i < NUM_SAMPLE_SCANS; i++)
{ start_tick = ticks_since_reset;

if( read_cmb_data( DIODE_ARRAY_CHAN, &ad_data[ 0]) == FAILURE)
        return( FAILURE);

j_scan = scan_index % NUM_TIME_TICKS;

/* CHECK SAMPLE TEMPERATURE & COVER OPEN STATUS */
    read_heater( &heater_data);
    if (fabs(37.0 - heater_data.temp) > 0.35)
        temp_cover_status[j_scan] = TEMP_STATUS_BIT;
    else
        temp_cover_status[j_scan] = 0;
    read_cover(&cover_status);
    if (Cover_status == COVER_OPENED)
        temp_cover_status[j_scan] |= COVER_STATUS_BIT;

for( j = 0; j < NUMBER_DATA_POINTS; j++)
        scan_data[j_scan][ j] = ad_data[ j];
    scan_index++;
```

*FIG. 22C*

```
edge_sel_pix_data( i ) = ad_data( eval_pixel);

edge_data += edge_sel_pix_data( i );

total_time = elapsed_time( start_tick, ticks_since_reset);

if( total_time < TIME_TICK_FREQ)
    wait( TIME_TICK_FREQ - total_time);

//*********************************************************//
//* Must Then Search For An Accumulation That Is < The Threshold *//
//*********************************************************//
for( i = 0; i < (NUM_EDGE_TICKS - NUM_SAMPLE_SCANS); i++)
{
    start_tick = ticks_since_reset;

if( edge_data < lead_edge_thresh)
    {
        consec_edge_cnt++;
        if (consec_edge_cnt >= MIN_CONSEC_EDGE_CNT)
        {
            edge_time_index = i;
            for( j = i + NUM_SAMPLE_SCANS; j < NUM_EDGE_TICKS; j++)
                edge_sel_pix_data( j ) = 0;

break;
        }
    }
```

FIG. 22D

```
else
{
    consec_edge_cnt = 0;
}
edge_data -= edge_sel_pix_data( i );

if( read_cmb_data( DIODE_ARRAY_CHAN, &ad_data[ 0 ]) == FAILURE)
    return( FAILURE );

j_scan = scan_index % NUM_TIME_TICKS;

/* CHECK SAMPLE TEMPERATURE & COVER OPEN STATUS */
read_heater( &heater_data );
if (fabs(37.0 - heater_data.temp) > 0.35)
    temp_cover_status[j_scan] = TEMP_STATUS_BIT;
else
    temp_cover_status[j_scan] = 0;
read_cover( &cover_status );
if (cover_status == COVER_OPENED)
    temp_cover_status[j_scan] |= COVER_STATUS_BIT;

for( j = 0; j < NUMBER_DATA_POINTS; j++)
    scan_data[ j_scan ][ j ] = ad_data[ j ];
scan_index++;
```

*FIG. 22E*

```c
        edge_sel_pix_data( i + NUM_SAMPLE_SCANS) = ad_data( eval_pixel);

edge_data += edge_sel_pix_data( i + NUM_SAMPLE_SCANS);

total_time = elapsed_time( start_tick, ticks_since_reset);

if( total_time < TIME_TICK_FREQ)
            wait( TIME_TICK_FREQ - total_time);
    } if( i >= (NUM_EDGE_TICKS - NUM_SAMPLE_SCANS))
    {
        edge_time_index = NUM_EDGE_TICKS;
        if (tst_error(CX_INSUFF_SAMP_ERR) == 0)
            set_error(CX_NO_SAMP_AT_SAMP_CHAMBER_ERR);
        return(FAILURE);
    }
    edge_scan_index = scan_index - NUM_SAMPLE_SCANS;
    leading_edge_overlap = NUM_SAMPLE_SCANS;
}
else
{
    for (i = 0; i < NUM_EDGE_TICKS; i++)
        edge_sel_pix_data(i) = 0;

edge_time_index = 0;
    edge_scan_index = 0;
    leading_edge_overlap = 0;
} ifdef DEBUG
    printf("\r\nSamp Reg\r\n");
    out_count = 0;
#endif
```

*FIG. 22F*

```
/****************************************************************/
/* Acquire Data For The Given Time Period.                      */
/****************************************************************/
for( i = 0; i < (NUM_TIME_TICKS - leading_edge_overlap); i++)
{
    start_tick = ticks_since_reset;

if( read_cmb_data( DIODE_ARRAY_CHAN, &ad_data[ 0]) == FAILURE)
        return( FAILURE);

j_scan = scan_index % NUM_TIME_TICKS;

/* CHECK SAMPLE TEMPERATURE & COVER OPEN STATUS */
    read_heater( &heater_data);
    if (fabs(37.0 - heater_data.temp) > 0.35)
        temp_cover_status[j_scan] = TEMP_STATUS_BIT;
    else
        temp_cover_status[j_scan] = 0;
    read_cover(&cover_status);
    if (cover_status == COVER_OPENED)
        temp_cover_status[j_scan] |= COVER_STATUS_BIT;

for( j = 0; j < NUMBER_DATA_POINTS; j++)
        scan_data[ j_scan][ j] = ad_data[ j];
    scan_index++;

total_time = elapsed_time( start_tick, ticks_since_reset);

if( total_time < TIME_TICK_FREQ)
        wait( TIME_TICK_FREQ - total_time);
}
```

*FIG. 22G*

```
/******************************************************//
/* Save The Single Pixel Information To Determine Where The Best Data Is. */
/******************************************************//
j_scan = edge_scan_index;

for( i = 0; i < NUM_TIME_TICKS; i++, j_scan++)
    samp_sel_pix_data[ i ] =
        scan_data[ j_scan * NUM_TIME_TICKS ][ eval_pixel ];

/******************************************************//
/* Determine Where The Best Data Resides. */
/******************************************************//
lowest_vr = SATURATED_SIGNAL * NUM_SAMPLE_SCANS;
samp_time_index = samp_index_index = lowest_vr_index = 0;
samp_index_2 = 0;

for( i = 0; i < (NUM_TIME_TICKS - NUM_SAMPLE_SCANS); i++)
{
    t_sum = samp_sel_pix_data[ i ];

vr = 0;
    for( j = 1; j < NUM_SAMPLE_SCANS; j++)
    {
        t_sum += samp_sel_pix_data[ i + j ];
        vr += abs( samp_sel_pix_data[ i ] - samp_sel_pix_data[ i + j ]);
    }
ifdef DEBUG
    if (out_count > 0 && (out_count % 3) == 0)
        printf("\r\n");
```

*FIG. 22H*

```
        printf("%3d/%6d       ", i, vr);
        out_count++;
#endif

/* Remember region with lowest vr even if > variability threshold,
           but don't remember any region that crosses leading edge thresh. */ if ( vr < lowest_vr && (lead_edge == DONT_FIND_LEAD_EDGE
                                || t_sum < lead_edge_thresh))
        {
            lowest_vr_index = i;
            lowest_vr = vr;
        }
        /* Remember all regions with vr < threshold and below L E Thresh. */
        if(lead_edge == DONT_FIND_LEAD_EDGE
           || t_sum < lead_edge_thresh)
        {
            if (vr < VAR_THRESHOLD)
                samp_region_index(samp_index_index++) = i;
            else if (vr < VAR_THRESHOLD_2)
                samp_region_index_2(samp_index_index_2++) = i;
        }
    } if (samp_index_index || samp_index_index_2)
    {
```

*FIG. 22I*

```
/*******************************************/
/* Look for region with lowest transmittance. */
/*******************************************/
lowest_sum = SATURATED_SIGNAL * NUM_SAMPLE_SCANS;
highest_sum = 0;
if (lowest_vr < VAR_THRESHOLD)
{
    index_index = samp_index_index;
    region_index = samp_region_index;
}
else
{
    index_index = samp_index_index_2;
    region_index = samp_region_index_2;
}
for (i=0; i<index_index; i++)
{
    jmax = (region_index(i) + NUM_SAMPLE_SCANS);
    sum = 0;
    for(j = region_index(i); j < jmax; j++)
        sum += samp_sel_pix_data(j);
    if (lead_edge == FIND_LEAD_EDGE)
    {
        if (sum < lowest_sum)
        {
            samp_time_index = region_index(i);
            lowest_sum = sum;
        }
    }
    else
    {
        if (sum > highest_sum)
        {
            samp_time_index = region_index(i);
```

FIG. 22J

```
          highest_sum = sum;
        }
      }
    }
  else           /* If nothing under vr threshold, use region with lowest vr. */
    {
    samp_time_index = lowest_vr_index;

if ( lowest_vr > (100*NUM_SAMPLE_SCANS))
      {
      switch(sample_info.sample_type)
        {
        case COOX_SAMP_BLOOD:
        case COOX_SAMP_QC:
          set_error(CX_BUBBLES_IN_SAMP_ERR);
          break;

case COOX_SAMP_SLOPE:
          set_error(CX_BUBBLES_IN_SLP_ERR);
          break;

case COOX_SAMP_ZERO:
          set_error(CX_BUBBLES_IN_ZERO_ERR);
          break;

default:
          break;
        }

BIT_PRINTF( "\r\nNO REGION with variability below %d !\r\n",
                  (200*NUM_SAMPLE_SCANS));
      return(FAILURE);
      }
    }
```

*FIG. 22K*

```
/*******************************************************************/
/* Initialize The Real Data Locations To Zero.                     */
/*******************************************************************/
data_start = data;
for( i = 0; i < NUMBER_DATA_POINTS; i++)
    *data_start++ = 0;

/*******************************************************************/
/* Accumulate The NUM_SAMPLE_SCANS Of Data Into The Real Data Locations. */
/* Also check that the sample chamber was at temperature and the cover was */
/* closed when the selected region was measured.                   */
/*******************************************************************/
status = SUCCESS;
for( i = samp_time_index; i < (samp_time_index + NUM_SAMPLE_SCANS); i++)
{
    data_start = data;
    j_scan = (i + edge_scan_index) % NUM_TIME_TICKS;
    if (sample_info.sample_type != COOX_SAMP_ZERO &&
        (temp_cover_status[j_scan] & TEMP_STATUS_BIT) != 0)
    {
        set_error(CX_COOX_SAMP_TEMP_OOR_ERR);
    } if ((temp_cover_status[j_scan] & COVER_STATUS_BIT) != 0)
    {
        status = FAILURE;
        if (sample_info.sample_type == COOX_SAMP_ZERO)
            set_error(CX_COVER_OPEN_ZERO_ERR);
        else
            set_error(CX_COVER_OPEN_MEAS_ERR);
    } for( j = 0; j < NUMBER_DATA_POINTS; j++)
        *data_start++ += scan_data[ j_scan ]( j );
} return( status );

/* END OF FUNCTION: READ_PROCESS_DATA
```

METHOD FOR PERFORMING SPECTROSCOPIC ANALYSIS OF INHOMOGENEOUS TEST SAMPLES

BACKGROUND OF THE INVENTION

1. Copyright Notice

A portion of the disclosure of this patent contains material which is subject to copyright protection. The owner has no objection to the reproduction by anyone of the patent document, but otherwise reserves all rights in copyright matter.

2. Technical Field

The present invention relates to an improvement for performing spectroscopic analysis of inhomogeneous test samples. More particularly, a plurality of signal measurements are performed on a test sample and analytical results are calculated only from a set of selected signal measurements most suited for giving reliable answers. The method of the present invention has particular application to the spectroscopic determination of the concentration of hemoglobin fractions or derivatives.

3. Technical Review

Spectroscopic measurement of fluids is a widely used technique for analytical chemistry. Apparatus for performing spectroscopic measurements are well-known in the art. The analysis of a test sample may be provided by moving the test sample into an optical cell and performing a transmittance, absorbance or reflectance measurement while the sample is stationery. Alternatively, a test sample may be flowed through an optical flow cell and a measurement taken while the sample is flowing through the optical cell. Optimally, such measurements are performed on non-scattering, homogeneous samples. Unfortunately, some samples contain inhomogeneities, such as air bubbles or particles, which make reliable measurements difficult. The presence of inhomogeneities in a test sample will, in some cases, adversely effect signal measurements requiring the sample to be rerun. More significantly, inhomogeneities will also cause subtle errors which may result in providing a test result which, although plausible, is, nevertheless, incorrect.

Accordingly, an object of the invention is to provide an improved method for performing spectroscopic analysis of inhomogeneous test samples.

A more specific object of the invention is to provide a method for improving transmittance, absorbance or reflectance measurements by selecting a specific set of signal measurements having low variability relative to the range or group of sample measurements or to a defined threshold to be used for analysis of a test sample.

Another object of the invention is to measure more accurately the concentration of hemoglobin fractions or derivatives in a blood sample.

It is another object of the invention to measure hemoglobin fractions or derivatives utilizing a new algorithm in conjunction with a spectrophotometer.

A further object of the invention is to compare and then select one or more sets of signal measurements provided by optical flow cell analysis of test samples to avoid signal measurements affected by test sample inhomogeneities.

The aforementioned object of the invention is achieved by the provision of a method of analyzing a plurality of optical cell signal measurements on a test sample; selecting from the measurements one or more sets of measurements having both low variability relative to the range or groups of signal measurements or a defined threshold and either signal level maxima or signal level minima; and utilizing the selected set of measurements to analyze the test sample.

Another object of the invention is to provide an algorithm for use in conjunction with a clinical laboratory instrument which is designed to perform many repetitive tests on unknown samples.

In a preferred embodiment of the invention, a series of transmittance, absorbance or reflectance signal measurements of a test sample are analyzed to select one or more sets of signal measurements having both low variability relative to the range or group of measurements or to a defined threshold and one of high or low transmittance, absorbance or reflectance signal levels for analyzing the test sample.

A further object of the invention is to provide a method for selecting a set of signal measurements from a spectroscopic analysis of a test sample, where homogeneous regions are selected by either using a temporal scan or a spatial scan of the test sample.

In another embodiment of the invention, a test sample is flowed through an optical flow cell to perform a series of transmittance measurements, a set of transmittance measurements are selected which have both low variability relative to the range or group of transmittance measurements or to a defined threshold and one of either transmittance maxima or transmittance minima, and then utilizing the mean value of the set of transmittance measurements to analyze the test sample.

4. Brief Description of the Drawings

The principal and a presently preferred embodiment of the invention will be described with reference to appended drawings in which:

FIG. 1 is a flow chart of the algorithm used in conjunction with spectroscopic analysis of test samples.

- FIG. 2A illustrates signals or ADC counts per unit time for an inhomogeneous test sample;
- FIG. 2B is an enlargement of the ADC counts per unit time of FIG. 2A showing a selected window having low signal variability; and
- FIG. 2C illustrates computed variability of the signal levels of the test sample of FIG. 2B and shows a selected window at approximately time unit 97 (x-axis);

- FIG. 3A illustrates signals or ADC counts per unit time for an inhomogeneous test sample;
- FIG. 3B is an enlargement of the ADC counts per unit time of FIG. 3A showing a selected window having low signal variability; and
- FIG. 3C illustrates computed variability of the signal levels of the test sample of FIG. 3B and shows a selected window at approximately time unit 78 (x-axis);

- FIG. 4A illustrates signals or ADC counts per unit time for an inhomogeneous test sample;
- FIG. 4B is an enlargement of the ADC counts per unit time of FIG. 4A showing a selected window having low signal variability; and
- FIG. 4C illustrates computed variability of the signal levels of the test sample of FIG. 4B and shows a selected window at approximately time unit 82 (x-axis);

Figure 5A:
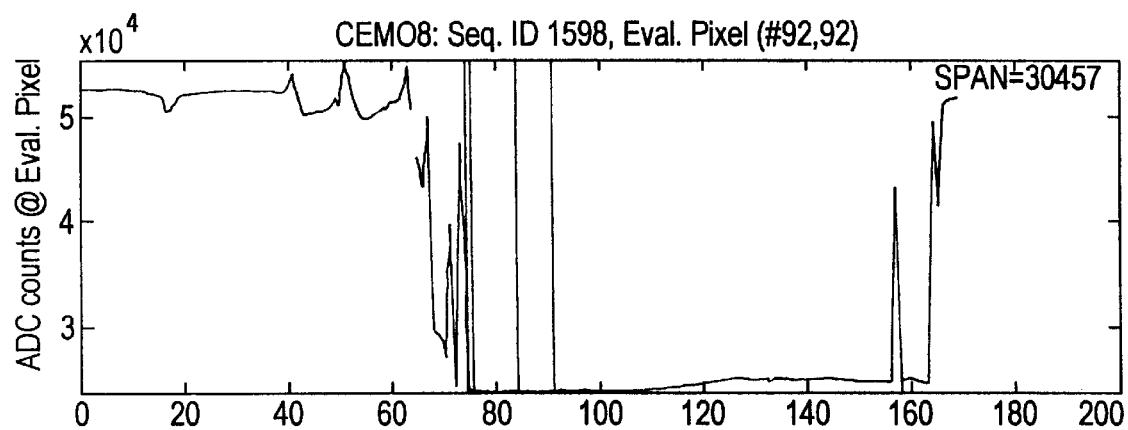
Figure 5B:
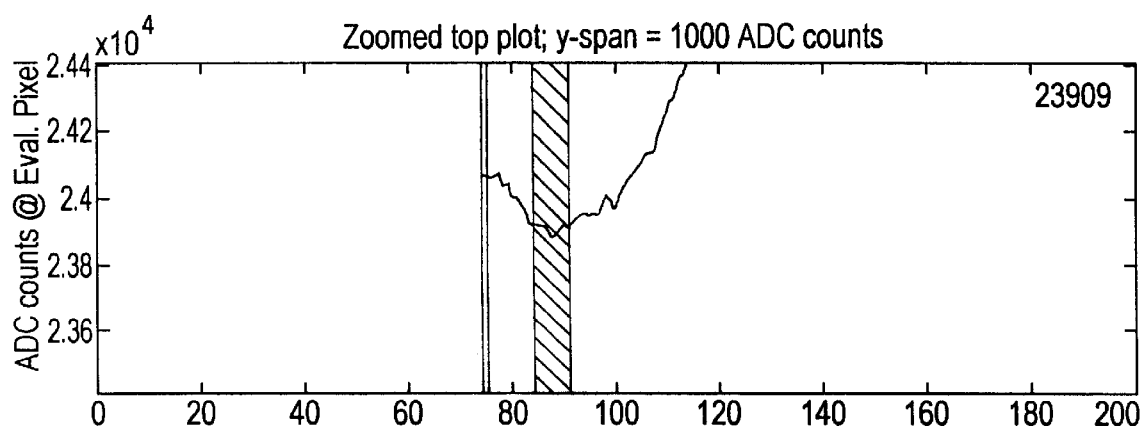
Figure 5C:
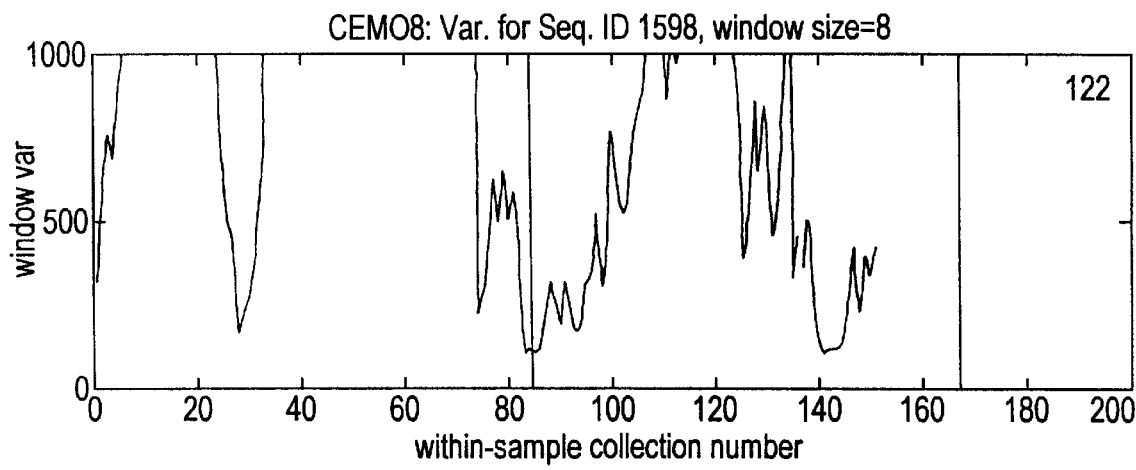
Figure 6A:
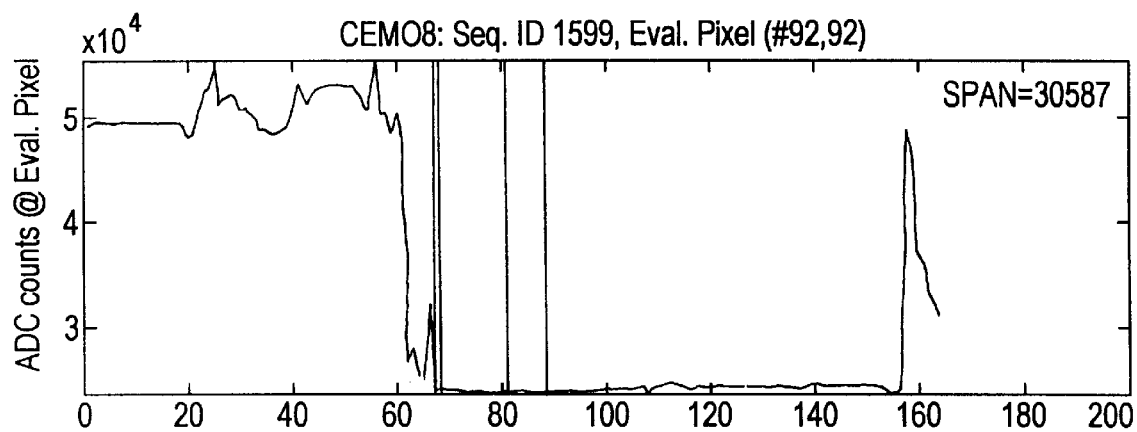
Figure 6B:
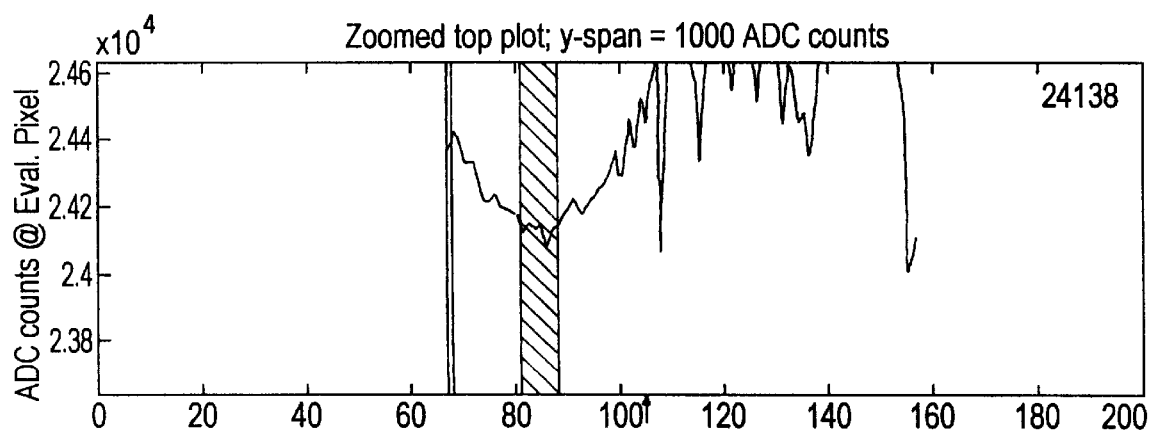
Figure 6C:
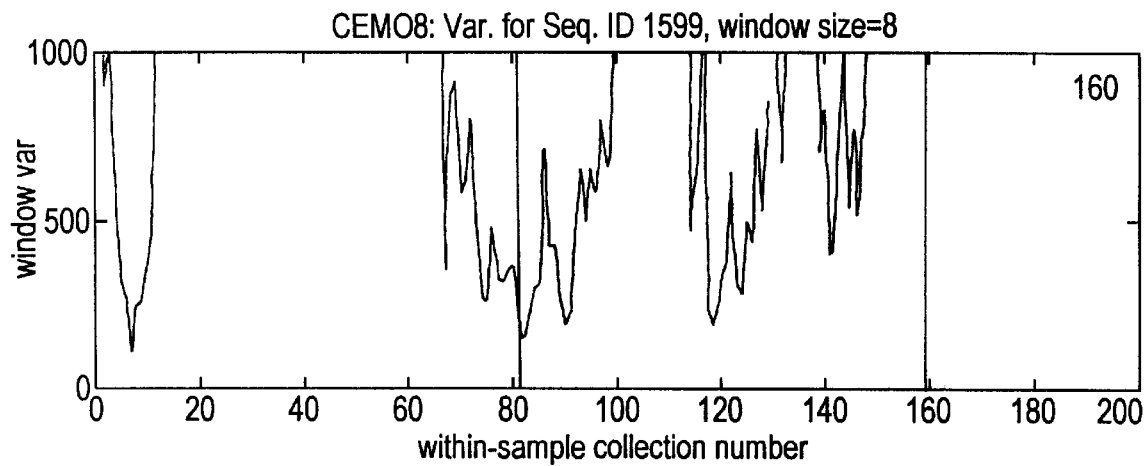
Figure 7A:
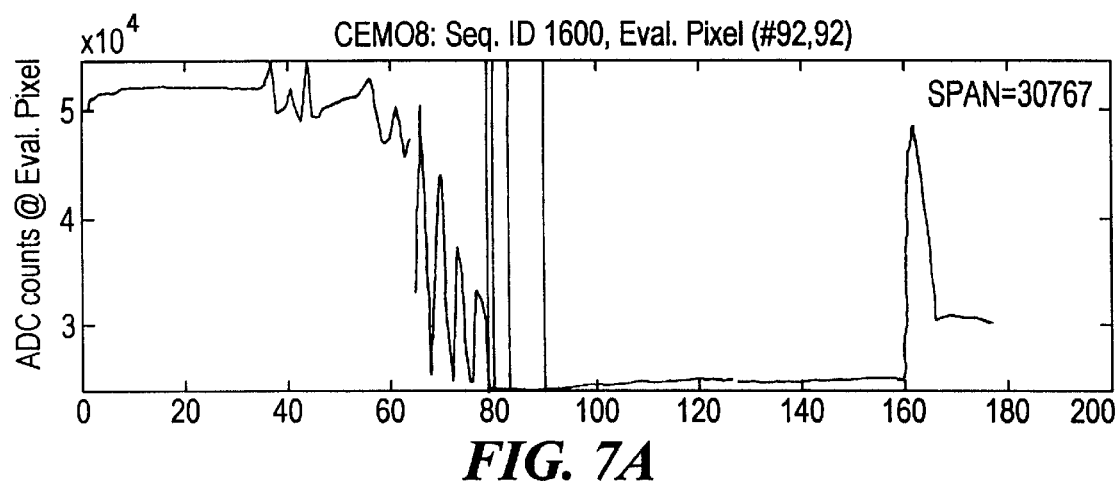
Figure 7B:
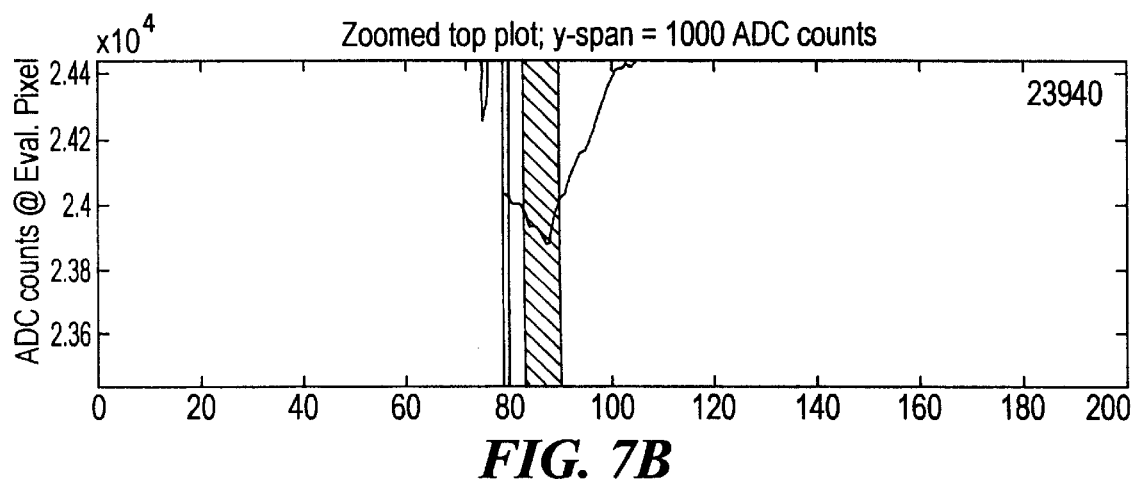
Figure 7C:
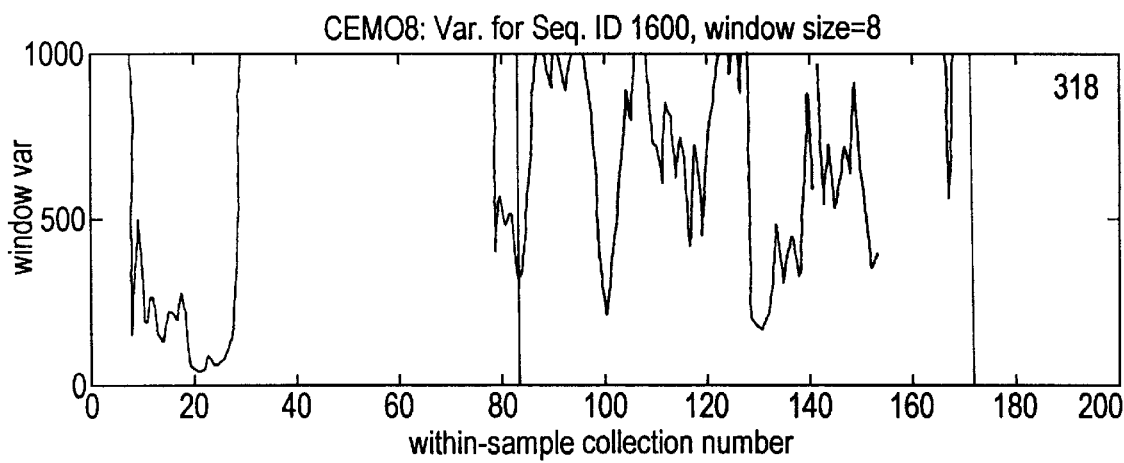
Figure 8A:
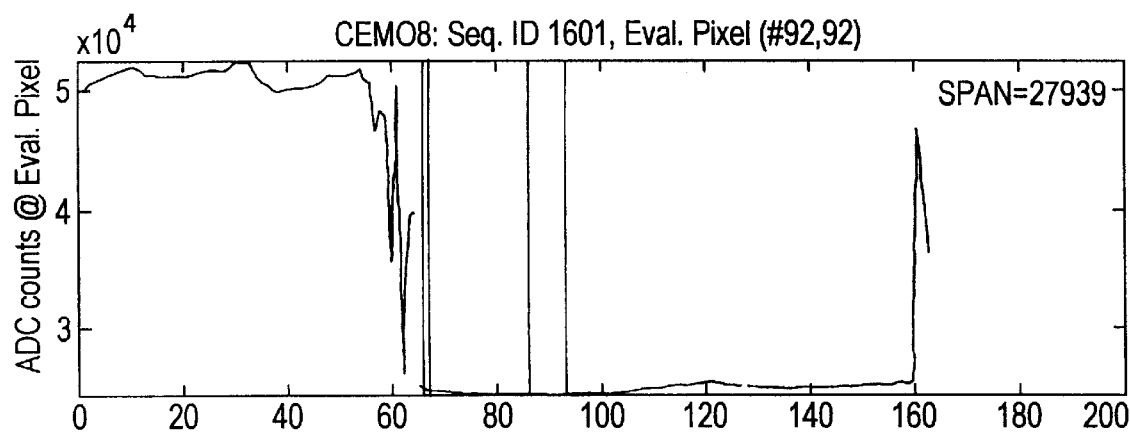
Figure 8B:
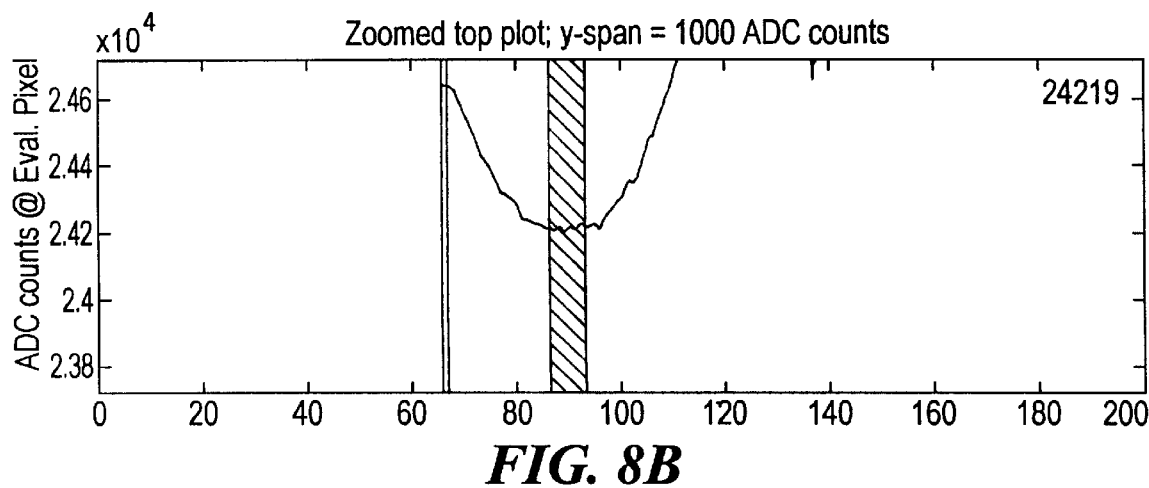
Figure 8C:
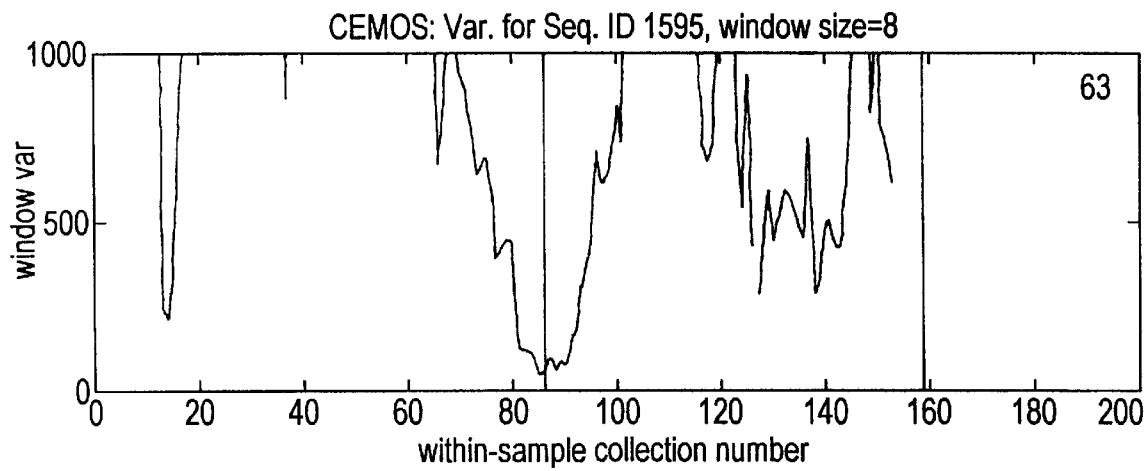
Figure 9A:
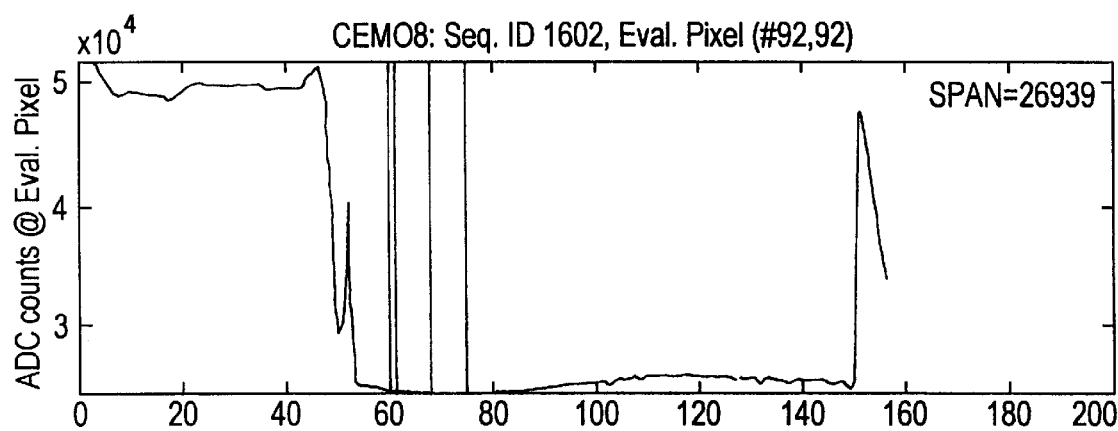
Figure 9B:
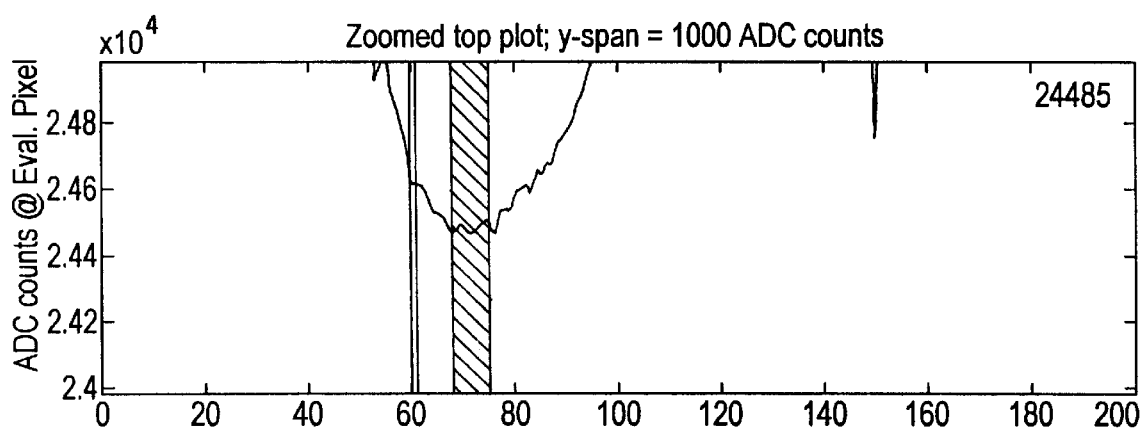
Figure 9C:
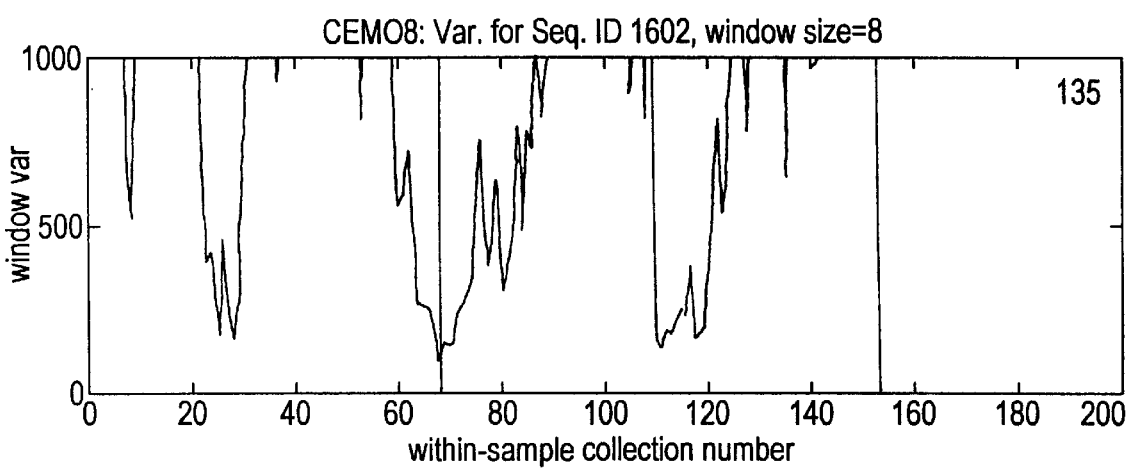
Figure 10A:
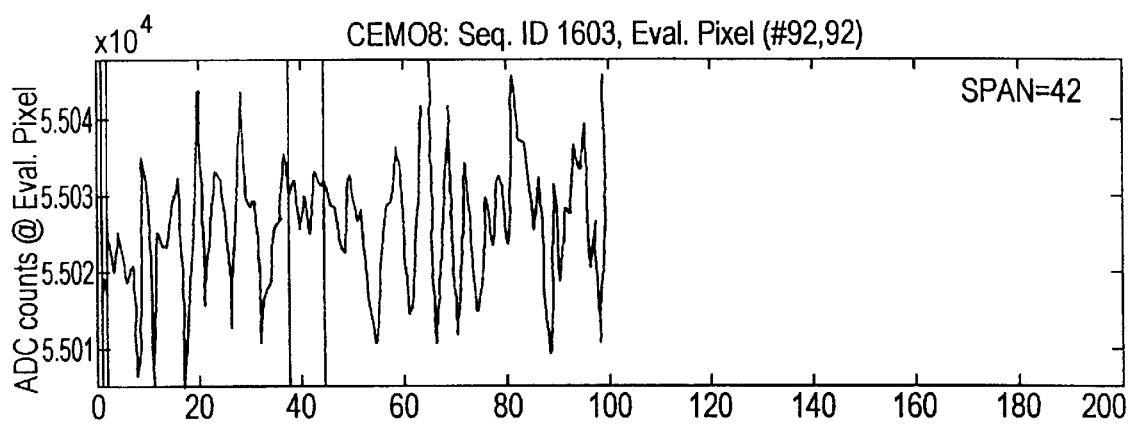
Figure 10B:
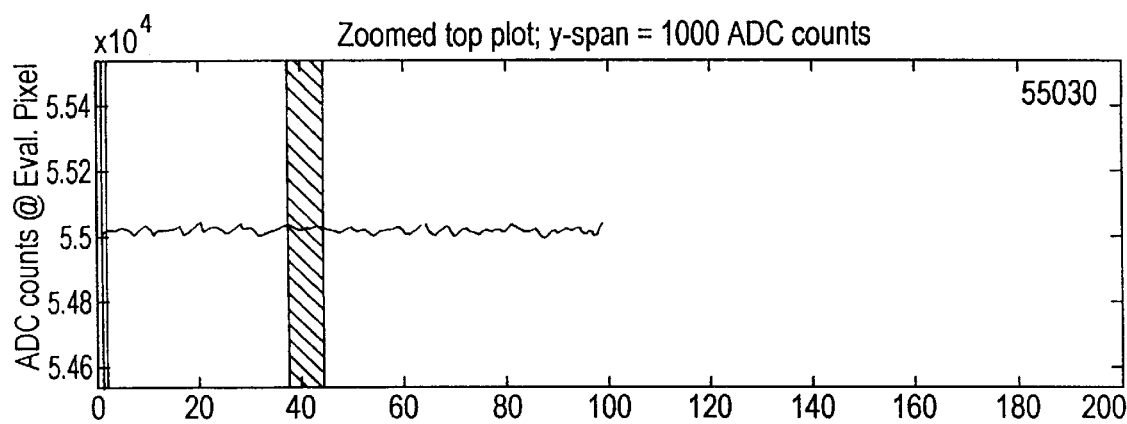
Figure 10C:
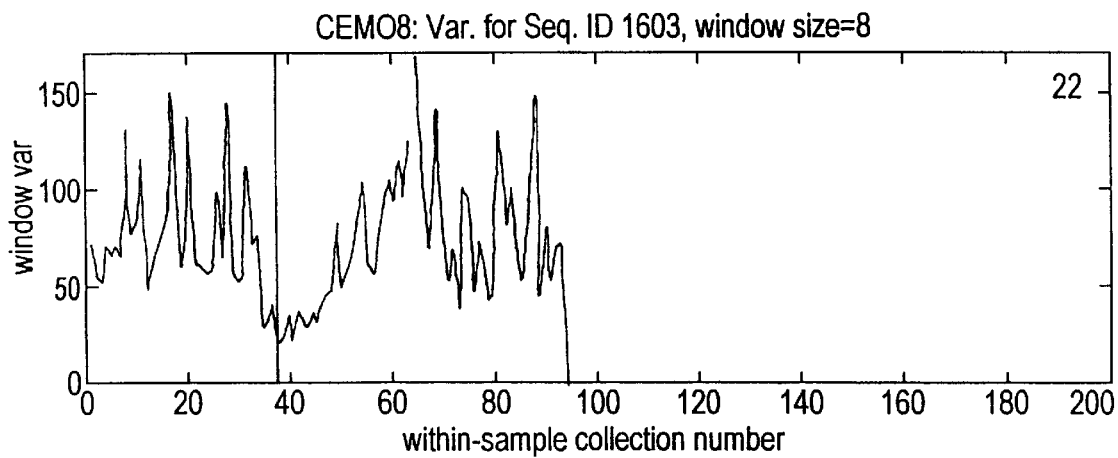
Figure 11A:
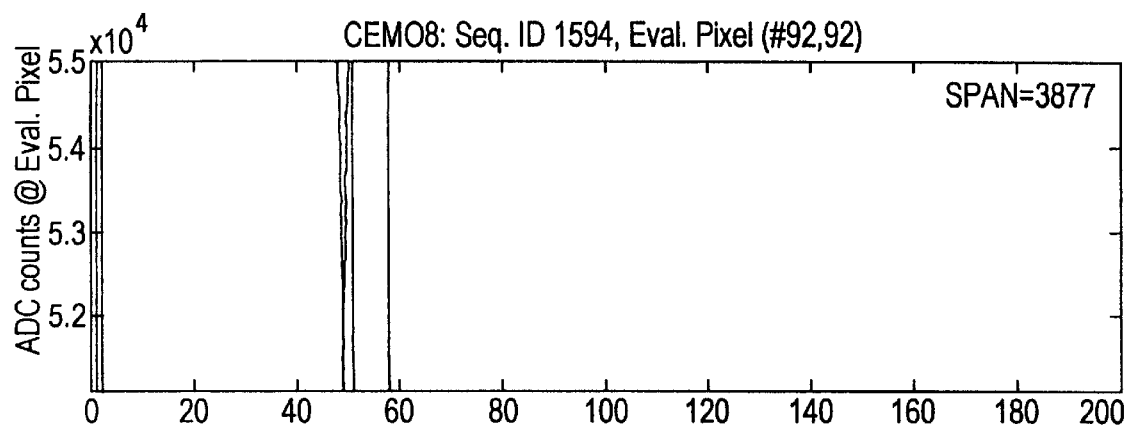
Figure 11B:
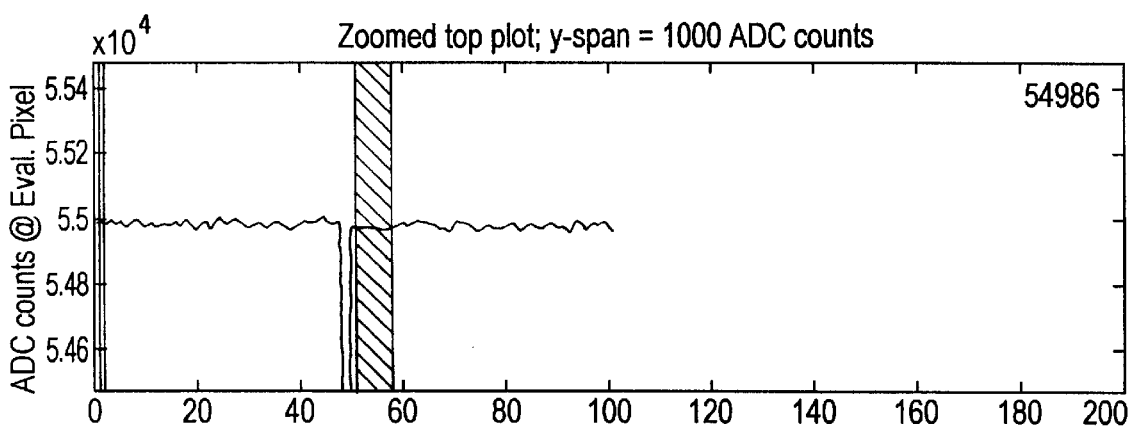
Figure 11C:
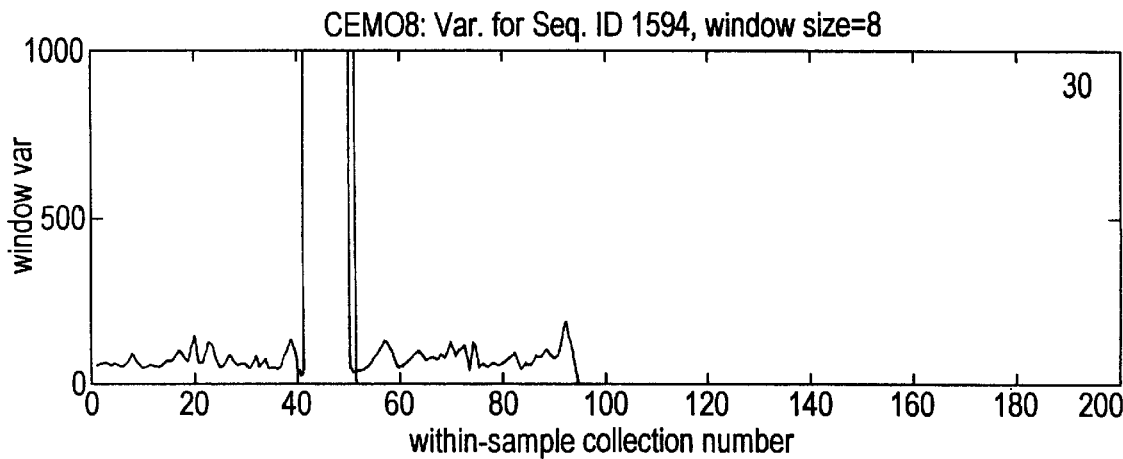
Figure 12A:
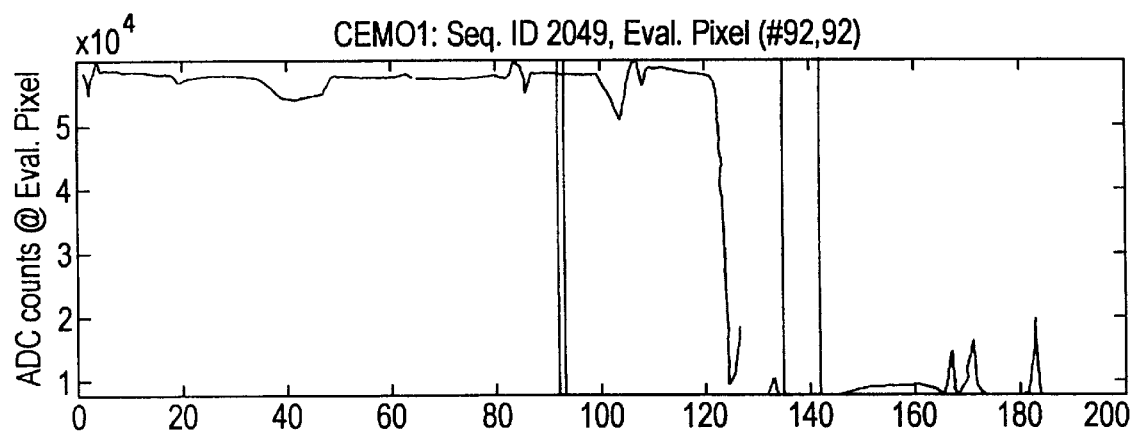
Figure 12B:
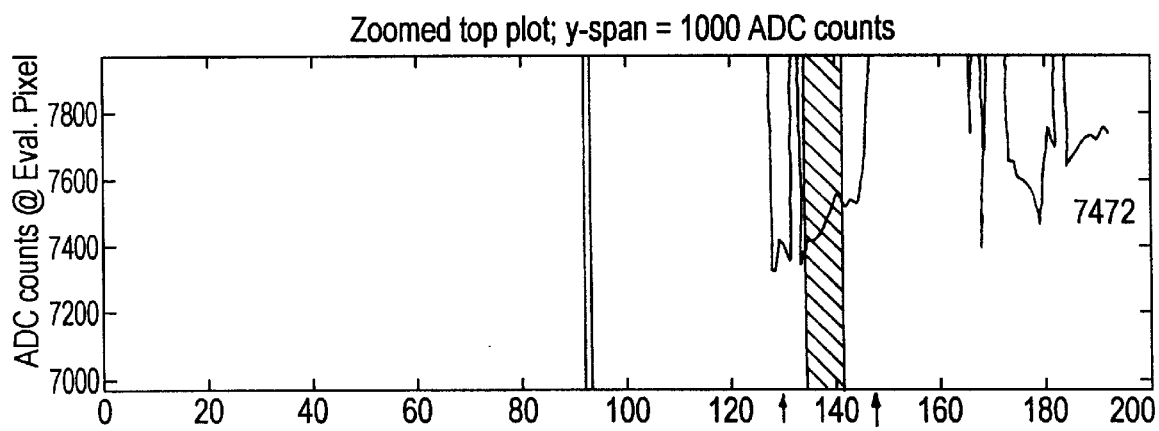
Figure 12C:
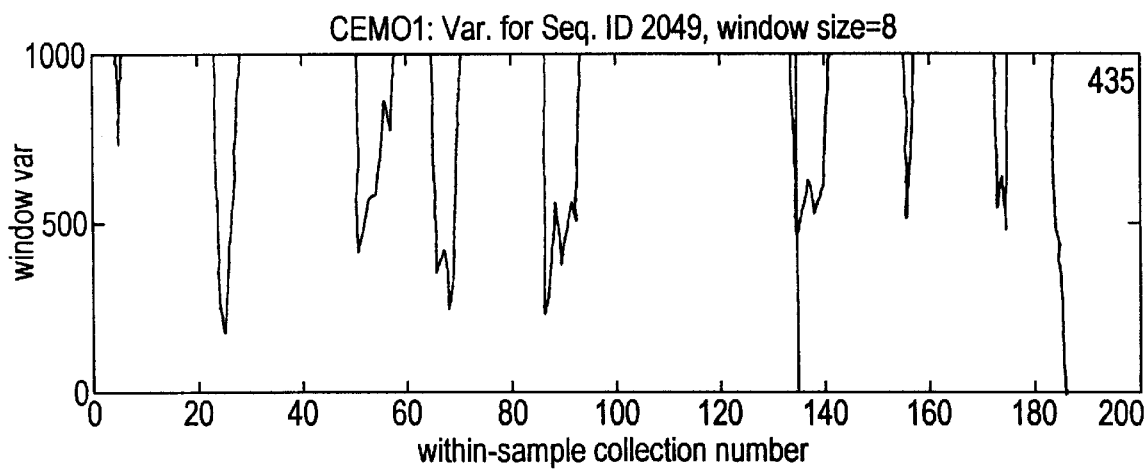
Figure 13A:
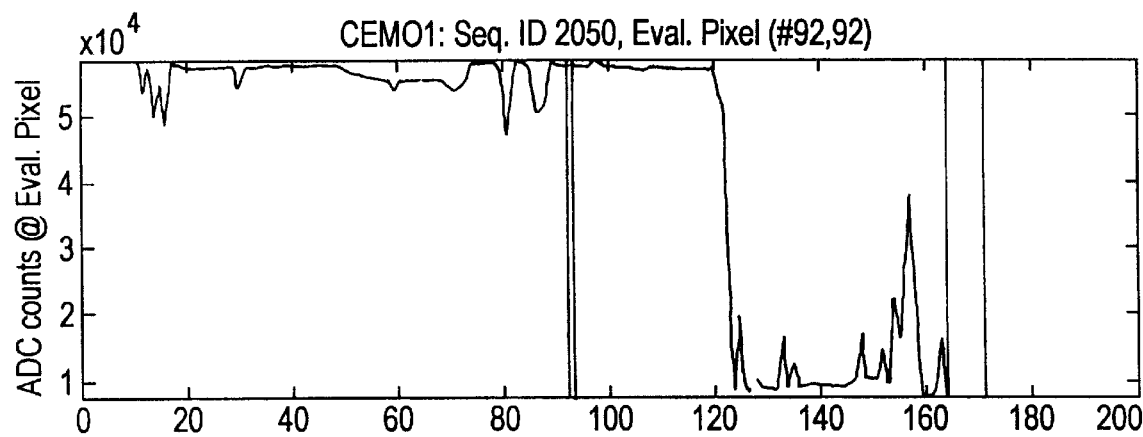
Figure 13B:
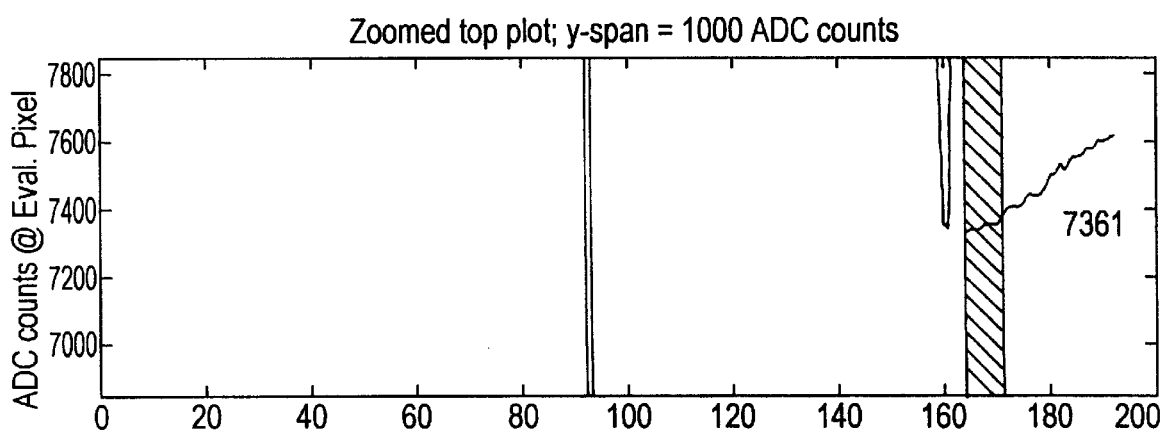
Figure 13C:
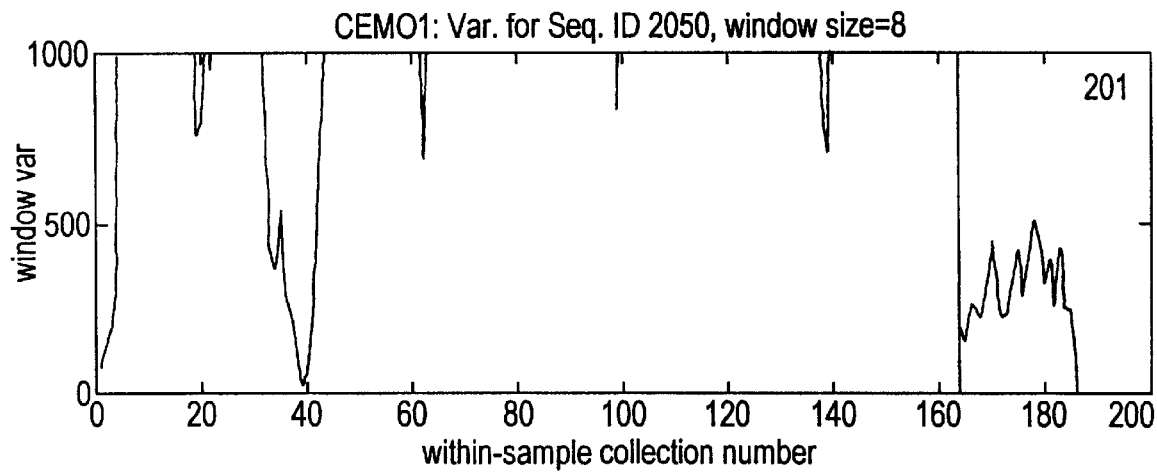
Figure 14A:
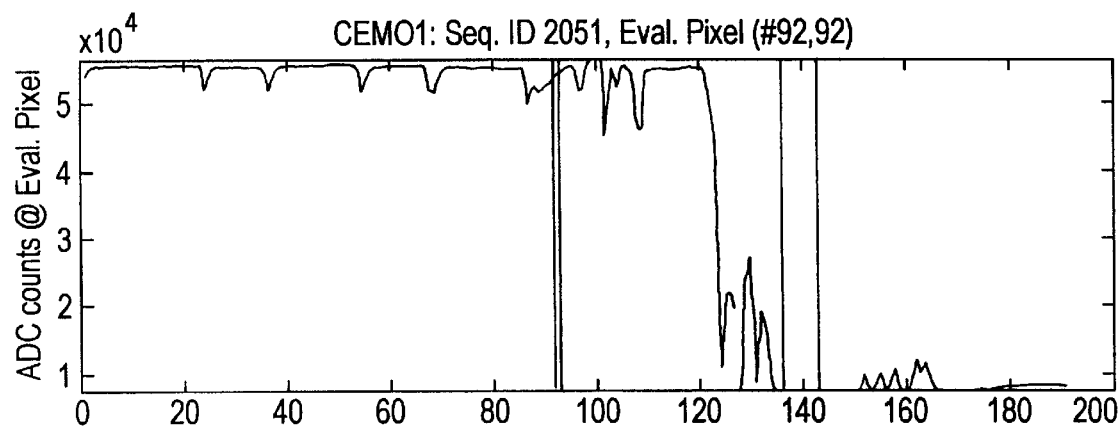
Figure 14B:
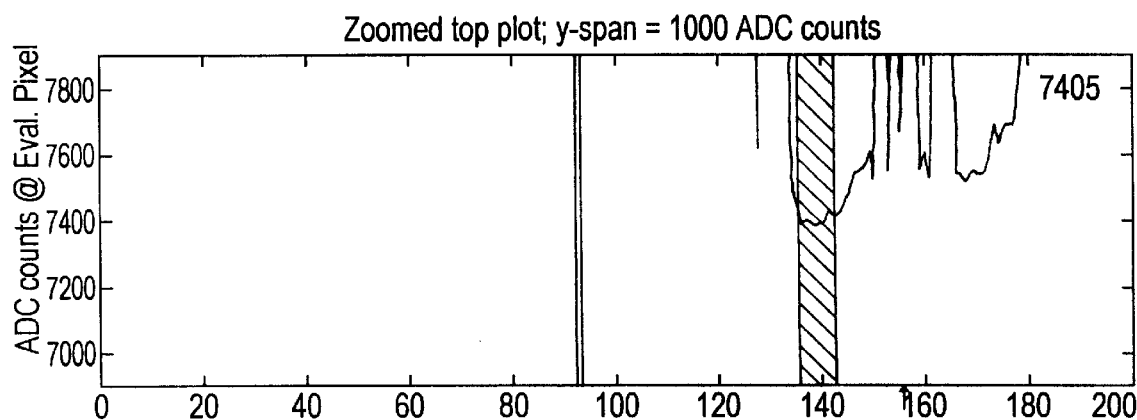
Figure 14C:
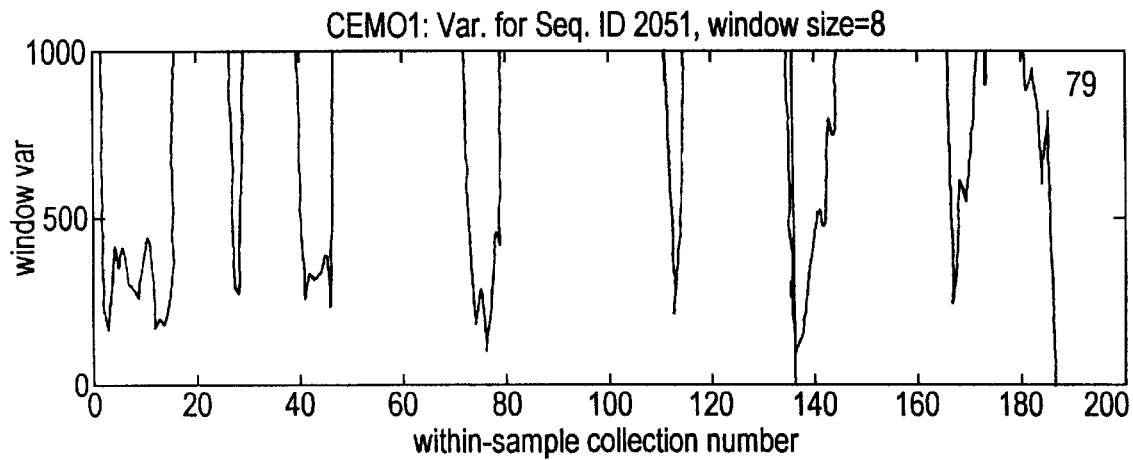
Figure 15A:
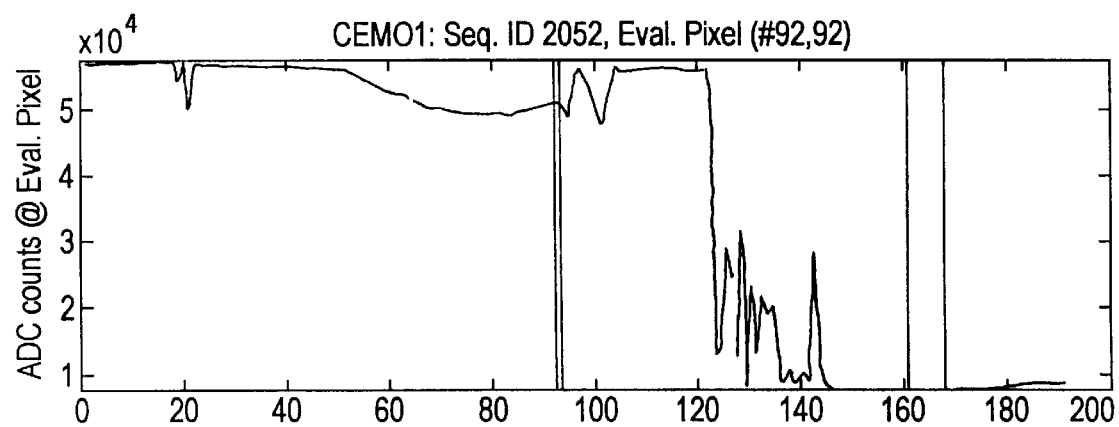
Figure 15B:
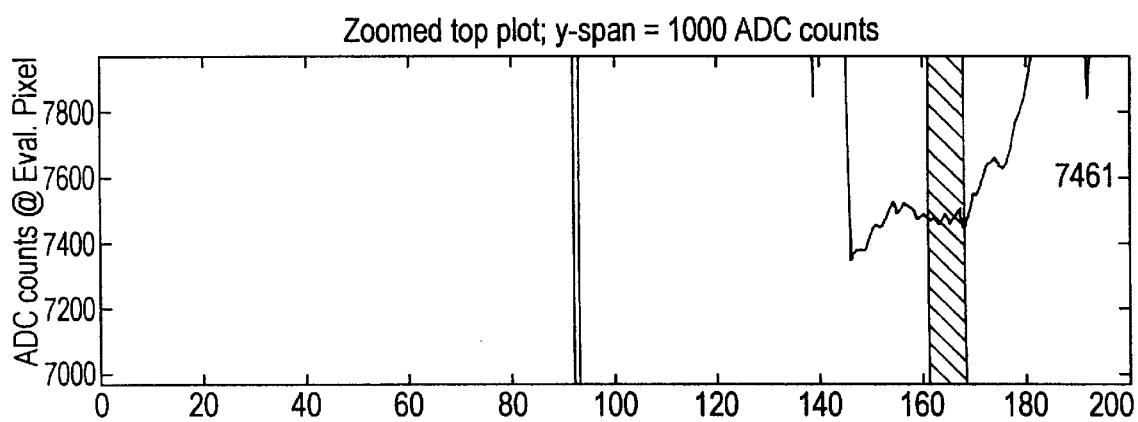
Figure 15C:
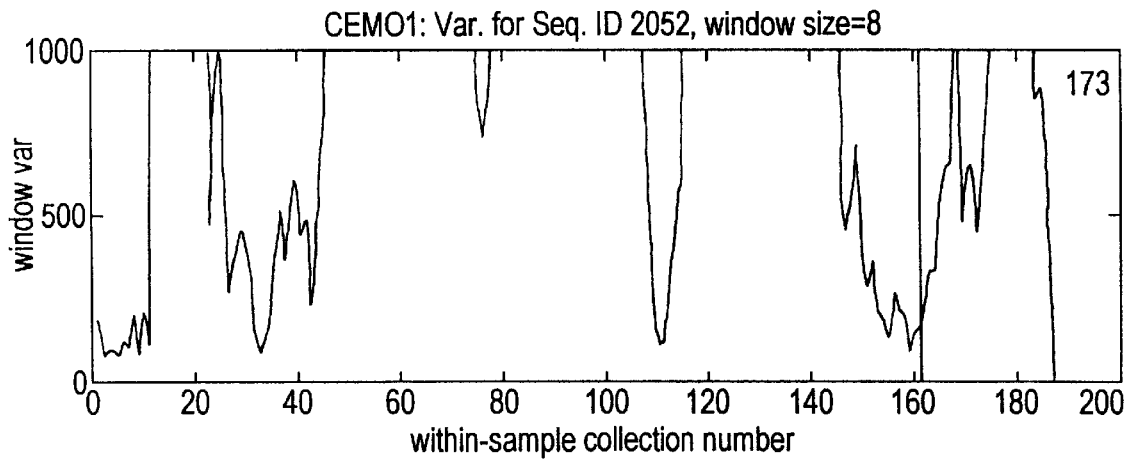
Figure 16A:
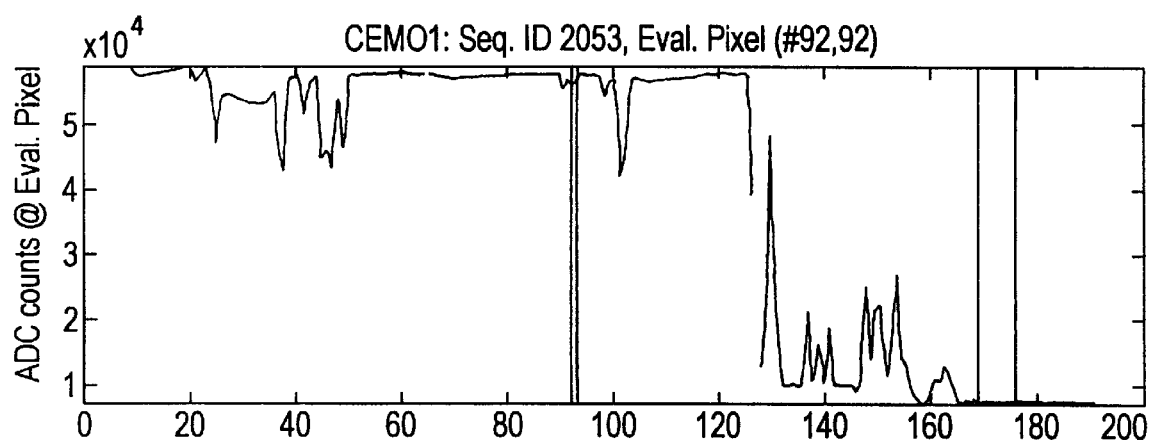
Figure 16B:
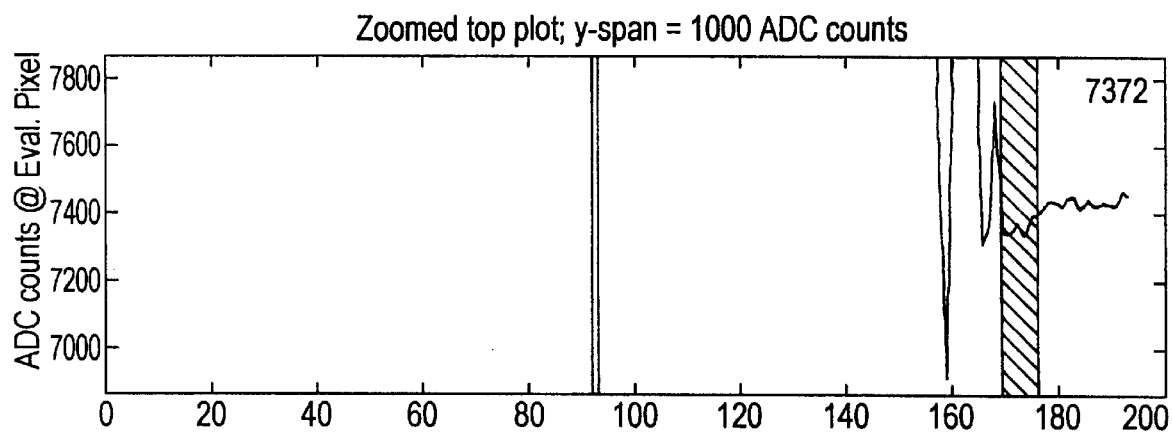
Figure 16C:
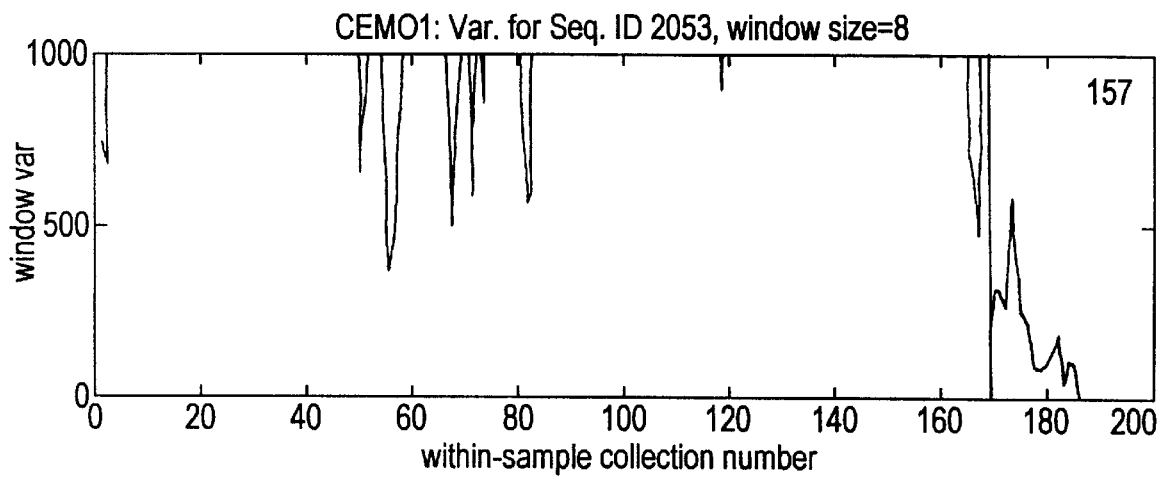
Figure 17A:
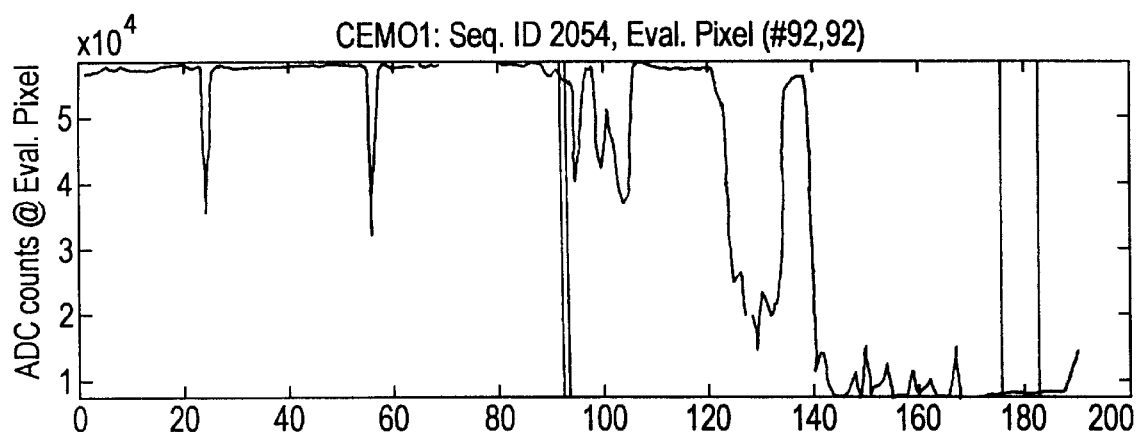
Figure 17B:
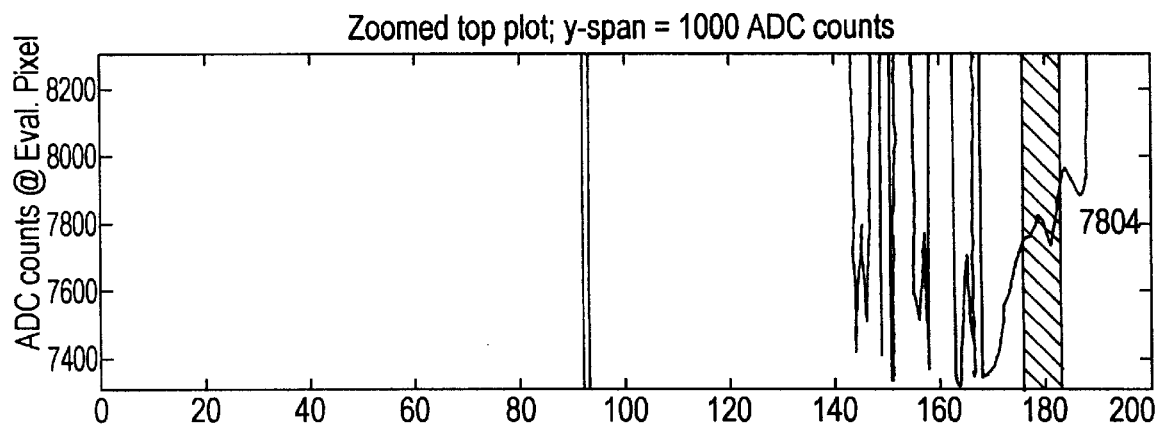
Figure 17C:
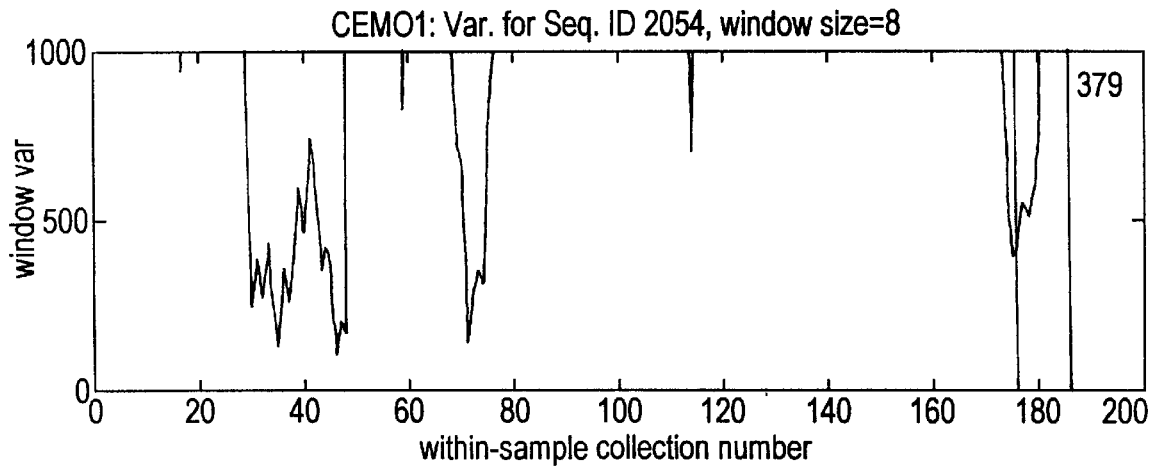
Figure 18A:
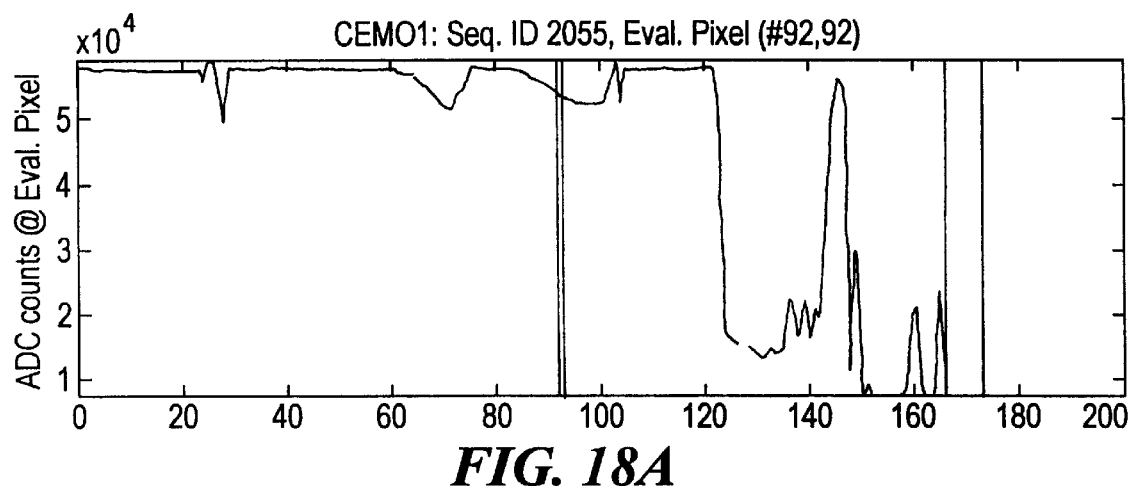
Figure 18B:
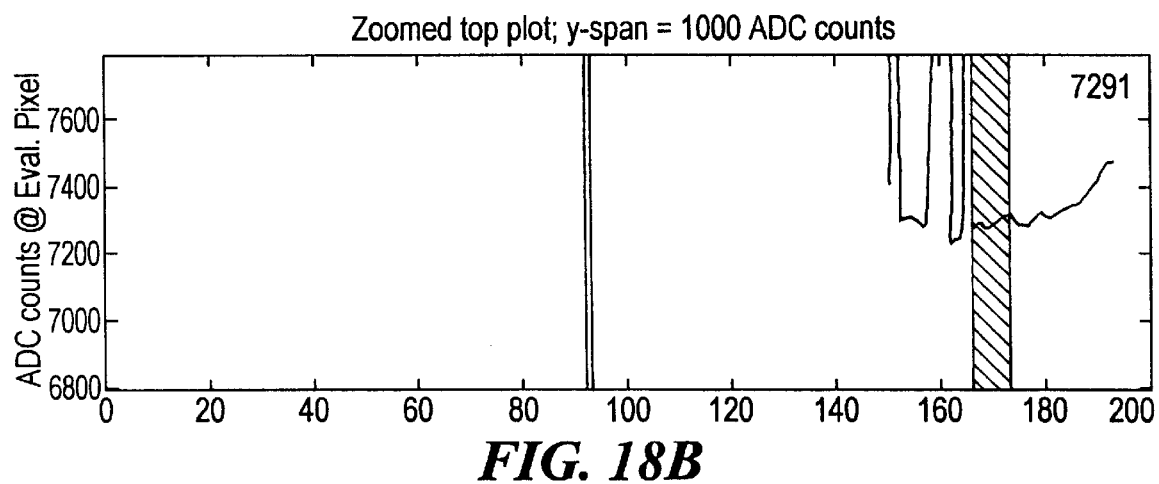
Figure 18C:
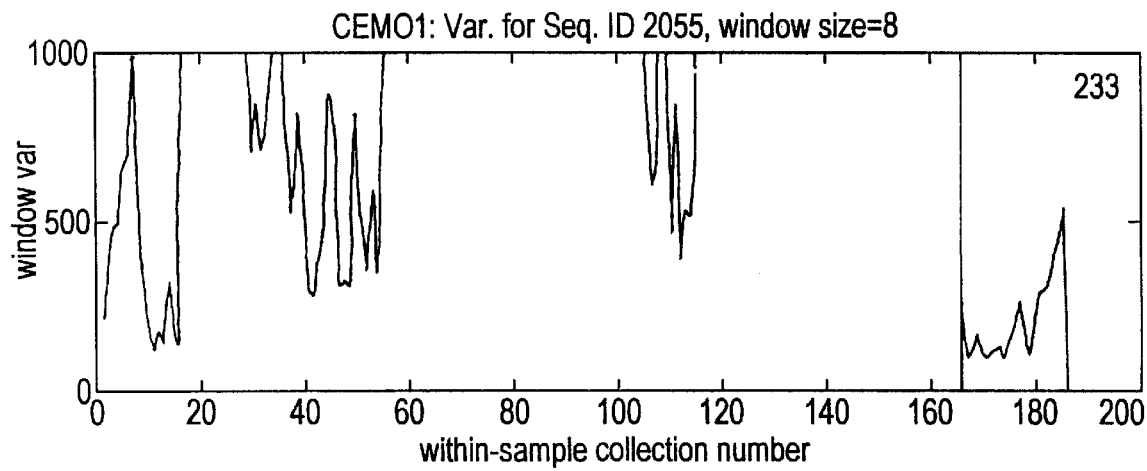
Figure 19A:
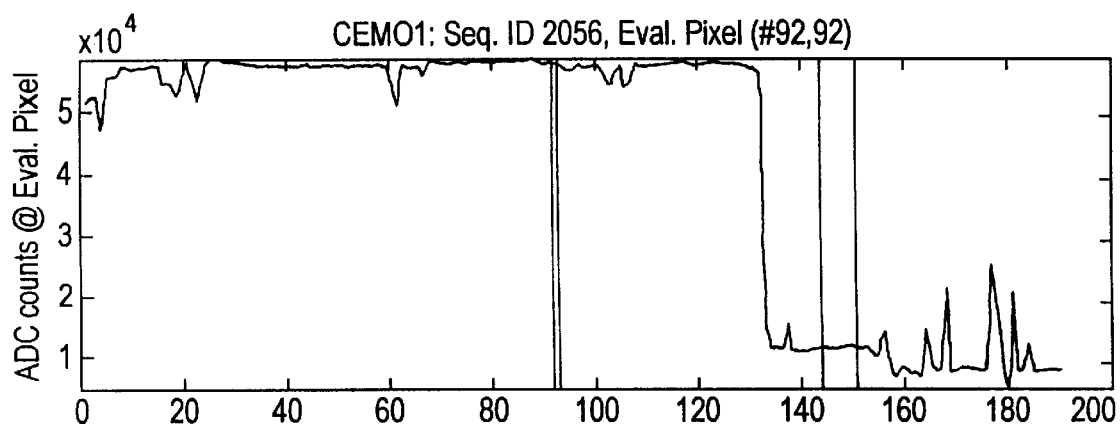
Figure 19B:
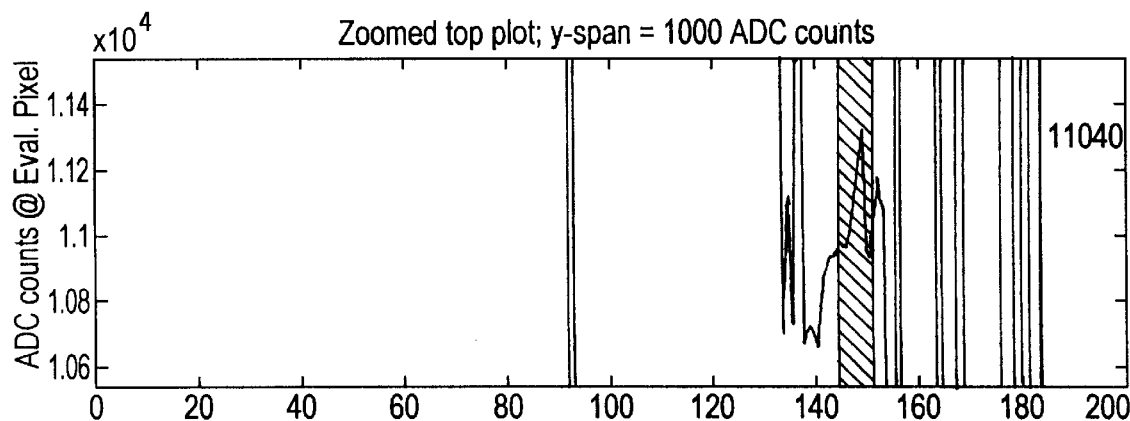
Figure 19C:
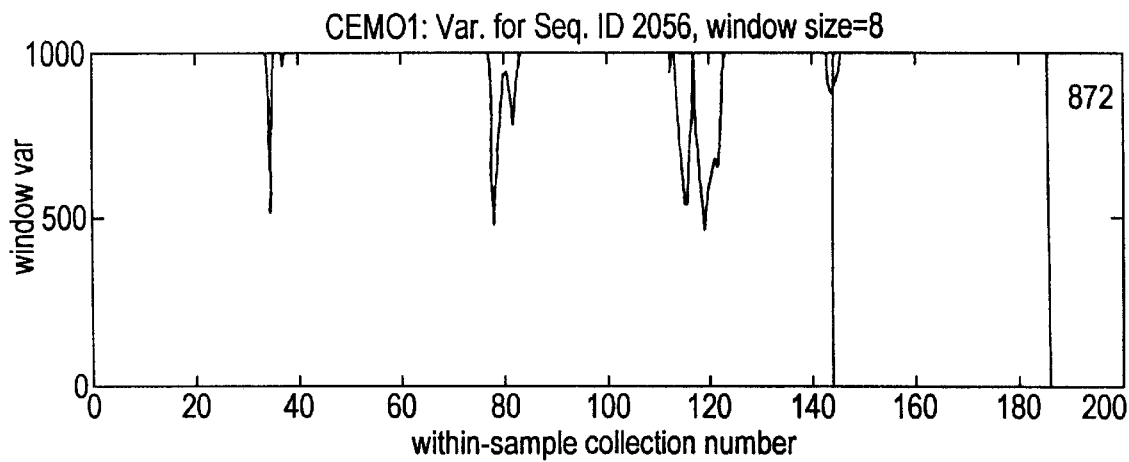
Figure 20A:
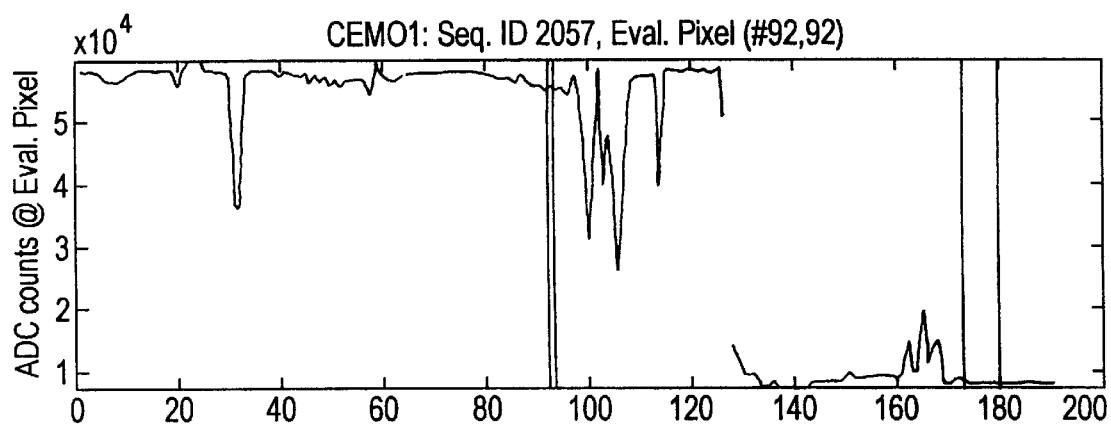
Figure 20B:
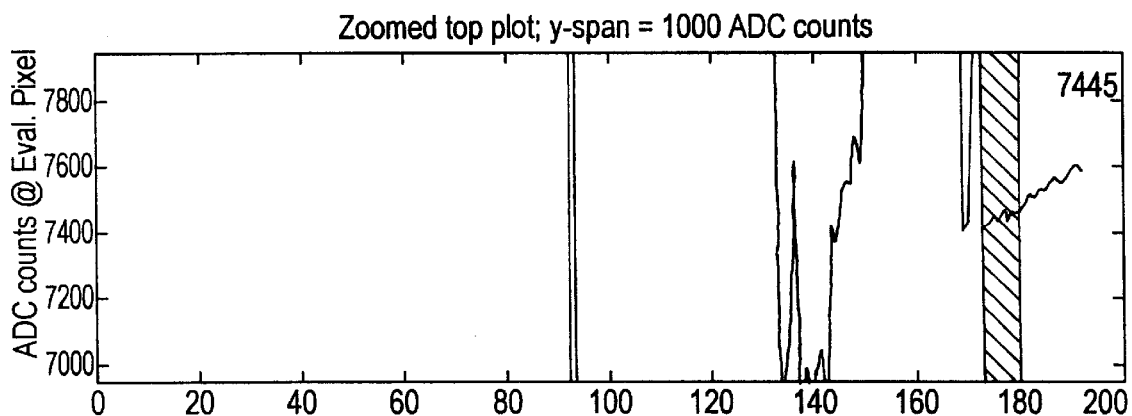
Figure 20C:
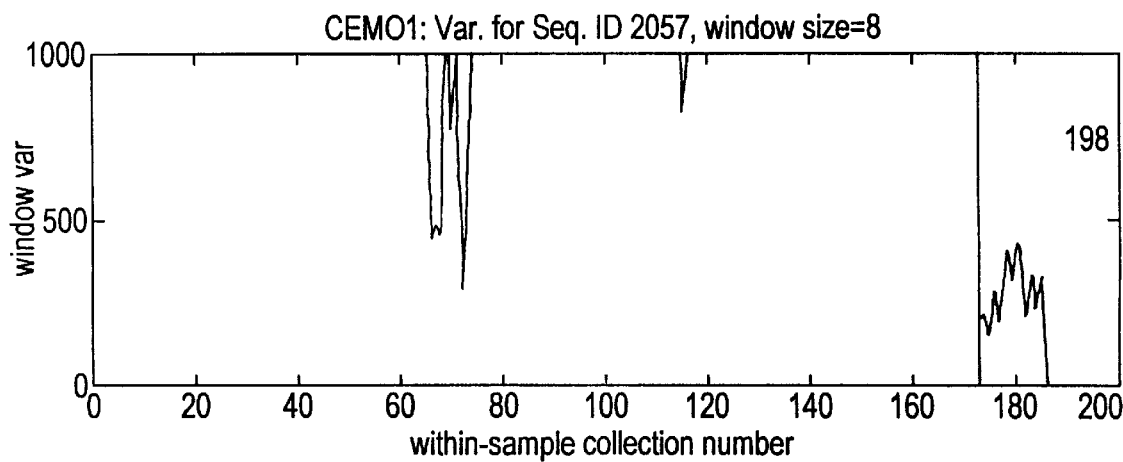
Figure 21A:
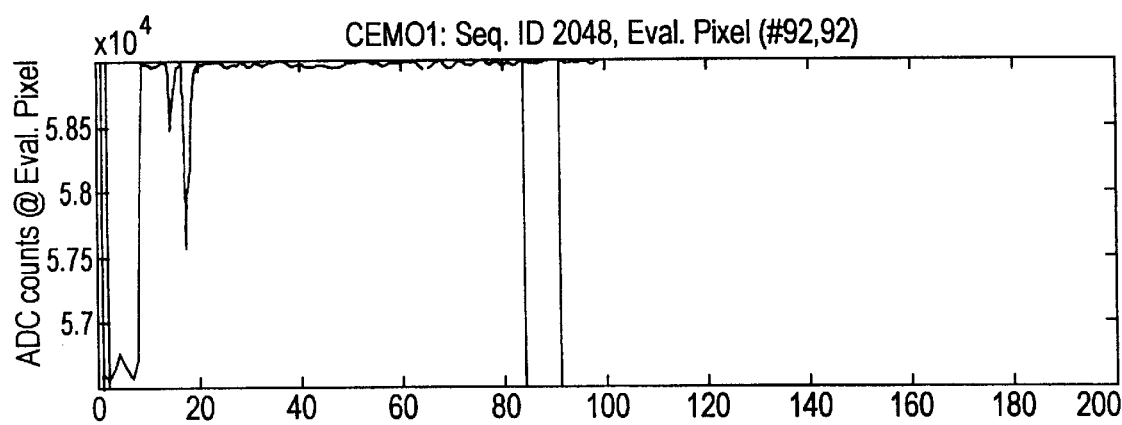
Figure 21B:
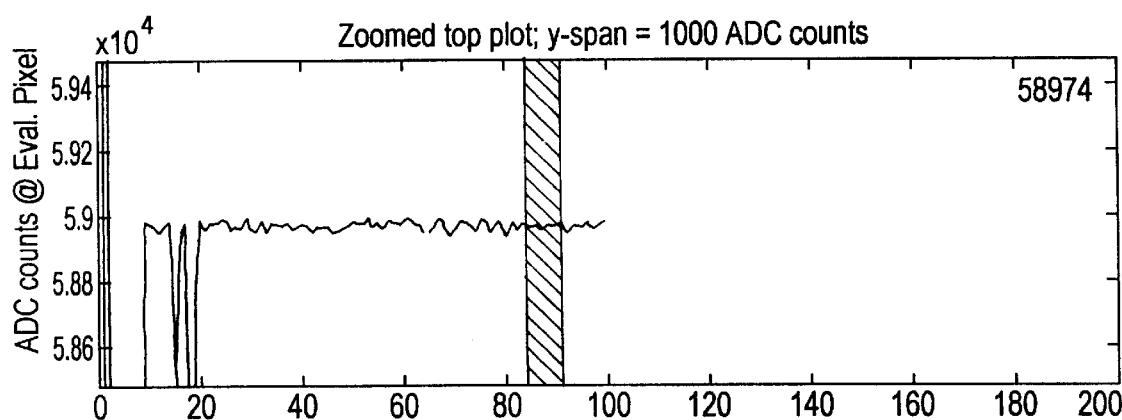
Figure 21C:
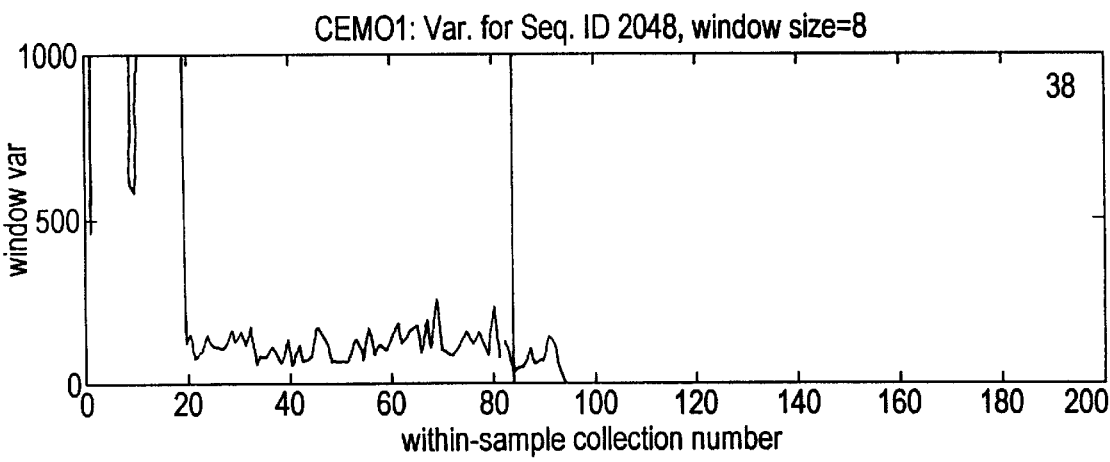
Figure 23:
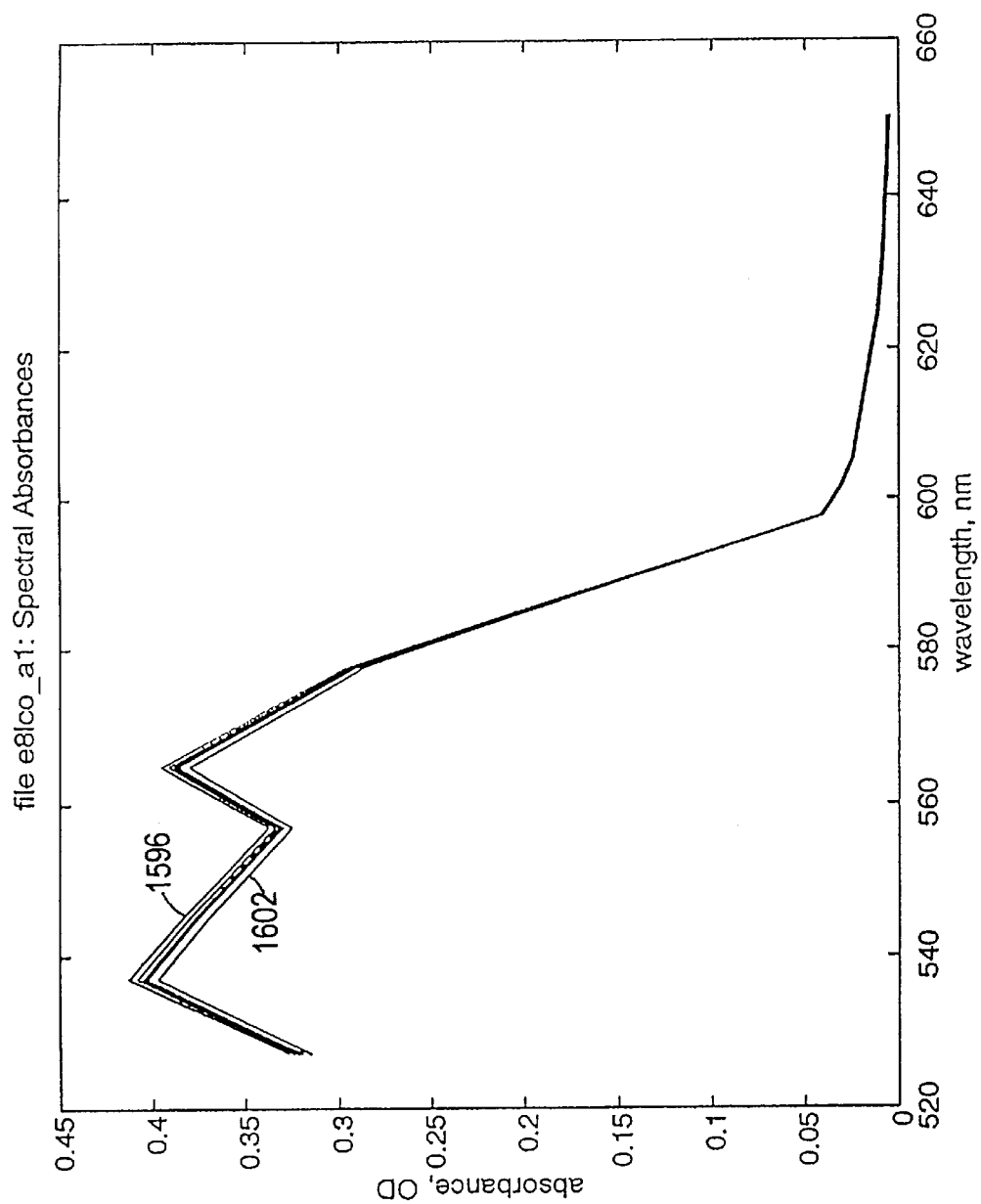
Figure 24:
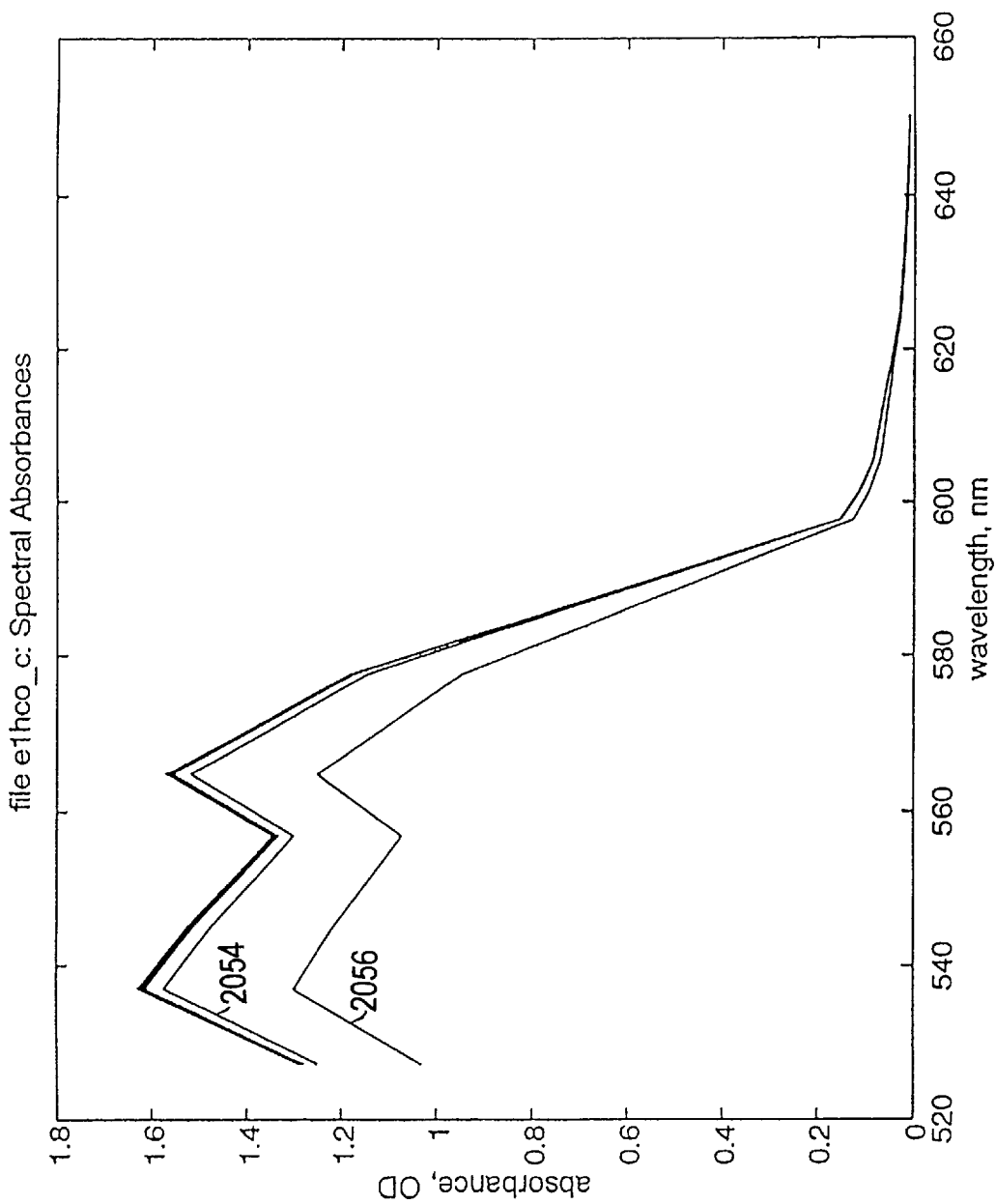

FIGS. 5A–5C illustrate signal readings for test sample 1598 where:
- FIG. 5A illustrates signals or ADC counts per unit time for an inhomogeneous test sample;
- FIG. 5B is an enlargement of the ADC counts per unit time of FIG. 5A showing a selected window having low signal variability; and
- FIG. 5C illustrates computed variability of the signal levels of the test sample of FIG. 5B and shows a selected window at approximately time unit 84 (x-axis);

FIGS. 6A–6C illustrate signal readings for test sample 1599 where:
- FIG. 6A illustrates signals or ADC counts per unit time for an inhomogeneous test sample;
- FIG. 6B is an enlargement of the ADC counts per unit time emission of FIG. 6A showing a selected window having low signal variability; and
- FIG. 6C illustrates computed variability of the signal levels of the test sample of FIG. 6B and shows a selected window at approximately time unit 82 (x-axis);

FIGS. 7A–7C illustrate signal readings for test sample 1600 where:
- FIG. 7A illustrates signals or ADC counts per unit time for an inhomogeneous test sample;
- FIG. 7B is an enlargement of the ADC counts per unit time of FIG. 7A showing a selected window having low signal variation; and
- FIG. 7C illustrates computed variability of the signal levels of the test sample of FIG. 7B and shows a selected window at approximately time unit 83 (x-axis);

FIGS. 8A–8C illustrate signal readings for test sample 1601 where:
- FIG. 8A illustrates signals or ADC counts per unit time for an inhomogeneous test sample;
- FIG. 8B is an enlargement of the ADC counts per unit time of FIG. 8A showing a selected window having low signal variability; and
- FIG. 8C illustrates computed variability of the signal levels of the test sample of FIG. 8B and shows a selected window at approximately time unit 85 (x-axis);

FIGS. 9A–9C illustrate signal readings for test sample 1602 where:
- FIG. 9A illustrates signals or ADC counts per unit time for an inhomogeneous test sample;
- FIG. 9B is an enlargement of the ADC counts per unit time of FIG. 9A showing a selected window having low signal variability; and
- FIG. 9C illustrates computed variability of the signal levels of the test sample of FIG. 9B and shows a selected window at approximately time unit 68 (x-axis);

FIGS. 10A–10C illustrate signal readings for a trailing blank test sample 1603 where:
- FIG. 10A illustrates signals or ADC counts per unit time for a trailing blank sample;
- FIG. 10B is an enlargement of the ADC counts per unit time of FIG 10A showing a selected window having low signal variability; and
- FIG. 10C illustrates computed variability of the signal levels of the test sample of FIG. 10B and shows a selected window at approximately time unit 38 (x-axis);

FIGS. 11A–11C illustrate signal readings for a leading blank sample 1594 where:
- FIG. 11A illustrates signals or ADC counts per unit time for a leading blank test sample;
- FIG. 11B is an enlargement of the ADC counts per unit time of FIG. 11A showing a selected window having low signal variability; and
- FIG. 11C illustrates computed variability of the signal levels of the test sample of FIG. 11B and shows a selected window at approximately time unit 52 (x-axis);

FIGS. 12A–12C illustrate signal readings for test sample 2049 where:
- FIG. 12A illustrates signals or ADC counts per unit time for an inhomogeneous test sample;
- FIG. 12B is an enlargement of the ADC counts per unit time of FIG. 12A showing a selected window having low signal variability; and
- FIG. 12C illustrates computed variability of the signal levels of the test sample of FIG. 12B and shows a selected window at approximately time unit 135 (x-axis);

FIGS. 13A–13C illustrate signal readings for test sample 2050 where:
- FIG. 13A illustrates signals or ADC counts per unit time for an inhomogeneous test sample;
- FIG. 13B is an enlargement of the ADC counts per unit time of FIG. 13A showing a selected window having low signal variability; and
- FIG. 13C illustrates computed variability of the signal levels of the test sample of FIG. 13B and shows a selected window at approximately time unit 163 (x-axis);

FIGS. 14A–14C illustrate signal readings for test sample 2051 where:
- FIG. 14A illustrates signals or ADC counts per unit time for an inhomogeneous test sample;
- FIG. 14B is an enlargement of the ADC counts per unit time of FIG. 14A showing a selected window having low signal variability; and
- FIG. 14C illustrates computed variability of the signal levels of the test sample of FIG. 14B and shows a selected window at approximately time unit 137 (x-axis);

FIGS. 15A–15C illustrate signal readings for test sample 2052 where:
- FIG. 15A illustrates signals or ADC counts per unit time for an inhomogeneous test sample;
- FIG. 15B is an enlargement of the ADC counts per unit time of FIG. 15A showing a selected window having low signal variability; and
- FIG. 15C illustrates computed variability of the signal levels of the test sample of FIG. 15B and shows a selected window at approximately time unit 162 (x-axis);

FIGS. 16A–16C illustrate signal readings for test sample 2053 where:
- FIG. 16A illustrates signals or ADC counts per unit time for an inhomogeneous test sample;
- FIG. 16B is an enlargement of the ADC counts per unit time of FIG. 16A showing a selected window having low signal variability; and
- FIG. 16C illustrates computed variability of the signal levels of the test sample of FIG. 16B and shows a selected window at approximately time unit 169 (x-axis);

FIGS. 17A–17C illustrate signal readings for test sample 2054 where:
  FIG. 17A illustrates ADC count per unit time for an inhomogeneous test sample;
  FIG. 17B is an enlargement of the ADC counts per unit time of FIG. 17A showing a selected window having low signal variability; and
  FIG. 17C illustrates computed variability of the signal levels of the test sample of FIG. 17B and shows a selected window at approximately time unit 176 (x-axis);

FIGS. 18A–18C illustrate signal readings for test sample 2055 where:
  FIG. 18A illustrates signals or ADC counts per unit time for an inhomogeneous test sample;
  FIG. 18B is an enlargement of the ADC counts per unit time of FIG. 18A showing a selected window having low signal variability; and
  FIG. 18C illustrates computed variability of the signal levels of the test sample of FIG. 18B and shows a selected window at approximately time unit 165 (x-axis);

FIGS. 19A–19C illustrate signal readings for test sample 2056 where:
  FIG. 19A illustrates signals or ADC counts per unit time for an inhomogeneous test sample;
  FIG. 19B is an enlargement of the ADC counts per unit time of FIG. 19A showing a selected window having low signal variability; and
  FIG. 19C illustrates computed variability of the signal levels of the test sample of FIG. 19B and shows a selected window at approximately time unit 144 (x-axis);

FIGS. 20A–20C illustrate signal readings for test sample 2057 where:
  FIG. 20A illustrates signals or ADC counts per unit time for an inhomogeneous test sample;
  FIG. 20B is an enlargement of the ADC counts per unit time of FIG. 20A showing a selected window having low signal variability; and
  FIG. 20C illustrates computed variability of the signal levels of the test sample of FIG. 20B and shows a selected window at approximately time unit 173 (x-axis);

FIGS. 21A–21C illustrate signal readings for a leading blank test sample 2048 where:
  FIG. 21A illustrates signals or ADC counts per unit time for a leading blank test sample;
  FIG. 21B is an enlargement of the ADC counts per unit time of FIG. 21A showing a selected window having low signal variation; and
  FIG. 21C illustrates computed variability of the signal levels of the test sample of FIG. 21B and shows a selected window at approximately time unit 83 (x-axis);

FIGS. 22A–22L is the code of a program for use on an analytical instrument for selecting signal measurements according to the algorithm of the present invention;

FIG. 23 is a diagram illustrating absorption spectra of test samples 1595–1602; and FIG. 24 is a diagram illustrating absorption spectra of test samples 2049–2057.

5. Detailed Description of the Invention

An algorithm is provided which, in conjunction with a spectrophotometer, makes possible simple and reliable analysis of inhomogeneous test samples. The algorithm teaches (a) finding a Leading Edge of the test sample; (b) collecting all data windows having signal variability below "Thresh 1"; (c) selecting data from one or more data windows satisfying (b) and a signal level criterion (lowest or highest from the set of data windows satisfying "Thresh 1"); (d) alternatively, if no data windows satisfy (b), collecting all data windows from one or more data windows having signal variability below "Thresh 2"; (e) selecting data from one or more data windows satisfying (d) and a signal level criterion (lowest or highest from the set of data windows satisfying "Thresh 2"); (f) alternatively, if no data windows satisfy (d), selecting data from one or more of the lowest variability windows; and (g) if selected data of (f) is greater than "Thresh 3" an error is declared.

The analysis of variance of test measurements is known in the art. Analysis of variance of signal measurements in the present invention is determined according to formula (1) as follows:

$$\text{Variability} = \sum_{i=2}^{n} abs(\text{data}_i - \text{data}_1) \qquad (1)$$

Alternate methods determining variability may be utilized to implement the above algorithm. The algorithm is written into a program for use on a computer in communication with or incorporated in a spectrophotometer to provide data analysis of signal measurements.

The Leading Edge is provided either (a) by setting a threshold at a specified value relative to the signal resulting from a blank sample or (b) setting a specified value as provided by (a) and further setting a signal variability criteria. In the preferred embodiment, the threshold for the Leading Edge is set at 80% of signal counts as determined by the blank sample.

Window size is optimally selected to avoid inhomogeneities of the sample while being large enough to provide a good measure of sample variability. Sample variability is a function of ADC (Analog to Digital Converter) counts or signals as best reflected by reference to the FIGS. In the preferred embodiment, the window size is set at eight (8) time units or time ticks, where at each time unit a signal measurement of the sample is performed. Each time unit of the preferred embodiment is equal to 0.1 second and each test sample is analyzed for 10 seconds. The time of analysis of a test sample is dependent, in part, on the sample size, the instrument utilized to perform measurements and the stability of the sample for analysis, any of which may vary while still utilizing the algorithm of the present invention.

In a fluid flow cell type spectrophotometer, instability may be reflected by bubbles in a test sample, a test sample being foamed, severely segmented or being diluted. The algorithm, as described above, provides the capability of selecting from an unsteady sample data for giving a reliable analysis of the sample. It is noted that in the utilization of the algorithm the stability of the signal measurements eventually becomes more important than high or low signal levels, i.e. low or high transmittance, absorbance or reflectance.

Each variability threshold is empirically set in accordance with the specifications or accuracy of the instrument or device utilized to perform the signal measurements and the window size which, in turn, is a function of the number of signals measured per unit time. The thresholds provide the criteria by which signal measurements may be utilized for test sample analysis. The values for the thresholds are set to provide a reasonable number of signal measurements for analysis before errors are noted in the results. Errors may be noted mathematically by converting signal measurements to absorbance for a known control and then assessing error. For example, "Threshold 1" may be set whereby at least 50% of the signal measurements can be used for analysis. "Threshold 2" may be set whereby at least 80% of the signal measurements can be used for analysis. In the spectrophotometer utilized in one embodiment of the invention, as provided by the b(low Examples, "Threshold 1" was set in the range of 200 to 400 variability units or 25 to 50 times the number of time units in the window. "Threshold 2" was set in the range of 400 to 800 variability units or 50 to 100 times the number of time units in the window. "Threshold 3" was set at in the range of 800 to 1600 variability units or 100 to 200 times the number of time units in the window. It is noted that where the variability of a sample being analyzed exceeds "Threshold 3", the measuring system will flag an error to the system controller. In the preferred embodiment, "Threshold 1" is set at 200 variable units; "Threshold 2" is set at 400 variable units; and "Threshold 3" is set at 800 variable units. It is noted that as the thresholds are decreased, a smaller number of signal measurements meet the variability criteria for selection. This means that more signal measurements will be characterized as outliers.

The thresholds provided in the algorithm also relate to the specifications or reliability of instrument performing the signal measurements. An instrument with higher accuracy will allow a lower "Threshold 3" to be set.

Data selection for the sample being analyzed first requires that a wavelength of maxium sensitivity be selected, for example, in the case of blood, a wavelength showing high absorbance, i.e. 577 nm. The selected wavelength will also be one where inhomogeneities in the sample will have the greatest effect.

In one embodiment of the present invention, the data set from a 256 channel optical detector spanning wavelengths 520–680 nm is analyzed relative to a wavelength or metric base selected, as noted above, based on maxium sensitivity to test sample inhomogeneities. One or more sets of measurement signals is selected according to the criteria defined by the algorithm. In a preferred embodiment, a single set of measurement signals or window is selected for sample analysis. Signal measurements are selected using either a temporal scan or spatial scan of the test sample. Optimally, in the case of a temporal scan of a flowing test sample, a plurality of serial signal measurements are analyzed.

In the analysis of a test sample by optical transmittance, a data set or window is selected by examining windows having both low variability and either maxium transmittance when the inhomogeneities decrease transmittance or minium transmittance when the inhomogeneities increase transmittance. The data from other measured wavelengths from the selected window is utilized for analysis of the test sample by use of appropriate equations as known in the art. In the case of hemoglobin fractions or derivatives, the wavelengths would be in range 520–680 nm. at which the hemoglobin fractions or derivatives have good absorption. Analysis from alternate wavelengths may be performed according to the analyte or component being evaluated in a test sample or for control purposes.

Referring to FIGS. 2B–21B, the window selected by use of the algorithm is shaded.

The chief advantage of the present method is that it makes the measurement subsystem of an analytical instrument, particularly a spectrophotometer, much less affected by inhomogeneities, i.e. bubbles or artifacts in the sample than previous systems. The reason is that in the preferred embodiment, the entire sample is measured a plurality of times and the test sample analysis is calculated only from a portion of the sample measurements most suitable for giving reliable answers. This means that if there are some bubbles in the sample, the portions of the sample with the bubbles will be avoided and only the best portion of the sample will be used to calculate results. In previous systems, the presence of inhomogeneities during the measurement would typically ruin the measurement of the test sample. Even worse, for some types of inhomogeneities, i.e. microbubbles, the error can be subtle, giving plausible but incorrect results that cannot be detected. The algorithm, defined by the present invention, also compensates for dilution in the system by selecting the least-diluted portion of the sample for measurement.

It is to be understood that the illustrations of signal measurements and the use of the algorithm flow diagram are to be interpreted as including functional representations of programs in a general purpose programmable computer used to accomplish the functions and operations described herein. Programmable computers and instrument operating systems can take various forms or configurations and the programming of such systems to accomplish the teaching of the present invention can also take many forms. Such variation in instruments or programming does not limit the use of the present invention. In the Examples below, a program is provided, see FIG. 22, for use on a co-oximeter to be marketed by Ciba Corning Diagnostics Corp.

In a preferred embodiment of the present invention, the algorithm is used in conjunction with an apparatus for spectrophotometrically determining the concentration of hemoglobin fractions or derivatives including tHb (total hemoglobin), $O_2Hb$ (oxyhemoglobin), HHb (deoxyhemoglobin), MetHb (methemoglobin), and COHb (carboxyhemoglobin).

The signals generated by the detectors of the spectrophotometer are analyzed using the algorithm of the present invention written in the form of a software program and executed on an appropriate computer, such as a microprocessor.

In the preferred embodiment, a 16-bit analog to digital converter is utilized having a measurement range of 100 ADC to 60K ADC counts. Signal variability, as described herein, is a function of ADC counts. The sample window size is also an important variable as a small window size will not allow a true measure of variability. While a smaller window size may be more adept at avoiding an inhomogeneity in the test sample, there is incumbent risk at not providing a true measure of variability of the sample.

In another embodiment, signal selection is used to determine groups or sets of signal measurements which contain only low variability within the group; and the selected groups are used to perform the sample analysis. Optimally, after these groups or sets are selected, the group having the lowest transmittance (or highest transmittance, depending on the inhomogeneity and sample) may also be chosen.

In analyzing the effect of the inhomogeneity on the test sample, the window will be selected utilizing maximum transmittance when the inhomogeneity decreases transmittance and, alternatively, choose a window having minimum transmittance when the inhomogeneity causes increased transmittance. For example, bubbles will, in general, increase transmittance in opaque fluids but will decrease transmittance in clear fluids. Particulate matter will typically decrease transmittance.

A specific application of the teaching of the present invention can be best described with reference to measuring the concentration of hemoglobin fractions in blood, as illustrated by the following Examples. The Examples are intended to illustrate and not to limit the invention and may be used as a guide by those skilled in the art to apply the principles of the present invention to other analytical uses.

6. Examples 1–10

A blood sample from a health voluntary donor was divided into nine (9) test samples, 1595–1602. Each sample was introduced into a prototype co-oximeter (800 series, Ciba Corning Diagnostics Corp.) for measurement of hemoglobin derivatives or fractions. The test sample is hemolyzed prior to entering a fluid flow cell for signal measurements (transmittance). Blank samples 1594 and 1603 consisting of an optically clear fluid were also analyzed. The signal measurements provided by the lead blank sample, 1594, are utilized in the determination of test sample transmittance.

Measurement signals for each test sample and blank were made at a series of times, every 0.1 sec. for 10 sec. for a total of 100 measurements or 100 time ticks. The measurements were divided into windows or segments of 8 points or 8 time ticks. The criteria for window size is based on the collection of signals which avoid inhomogeneities in the test sample and the flow rate of the sample past the detector or the portion of measurable sample or passage through the optical flow cell. Signal measurements for test samples 1595–1602 and blanks 1594 and 1603 are provided in FIGS. 2–11, respectively, illustrating ADC counts per time unit for the test samples. The window chosen by the algorithm for the sample or blank is shown in the shaded area of each respective figure. The mean value of the data provided in the window is utilized to calculate the concentration of hemoglobin derivatives or fractions.

Figure 2A:
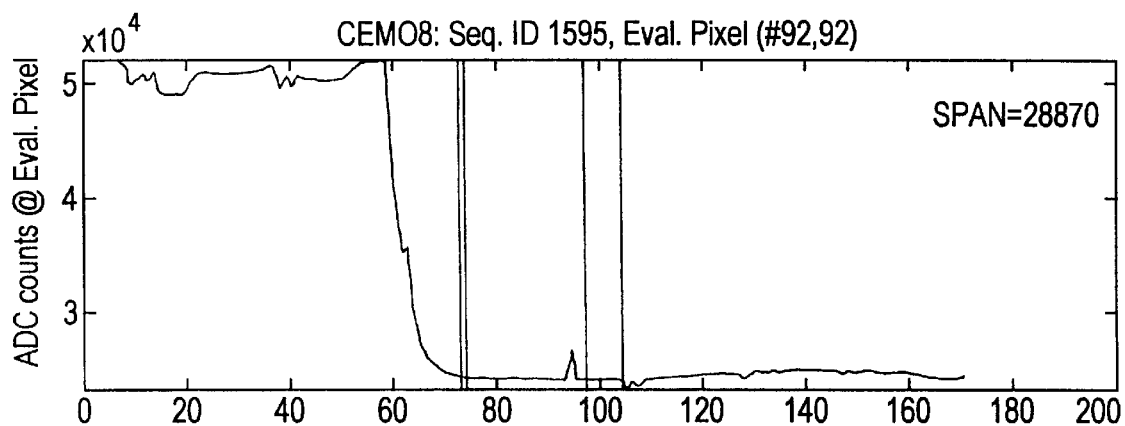
FIGS. 2A–2C illustrate signal readings for test sample 1595 where.
Figure 2B:
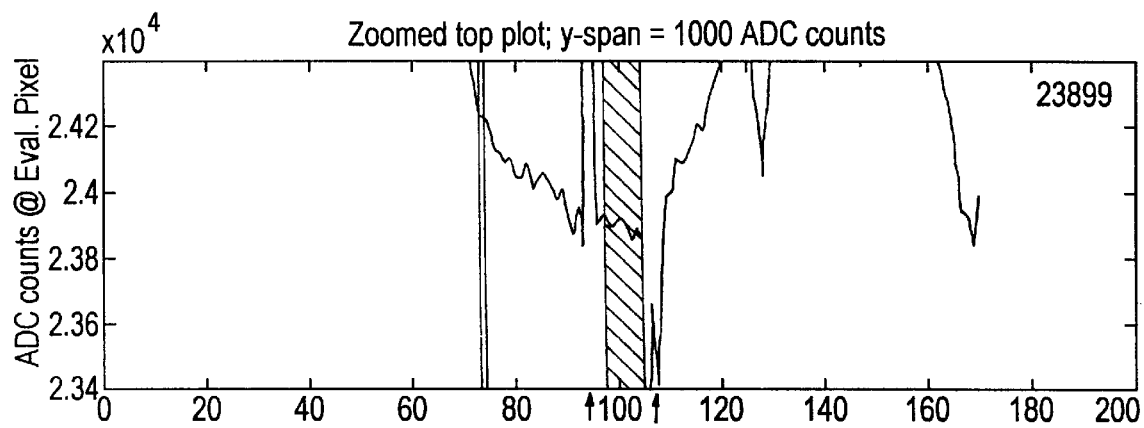
Figure 2C:
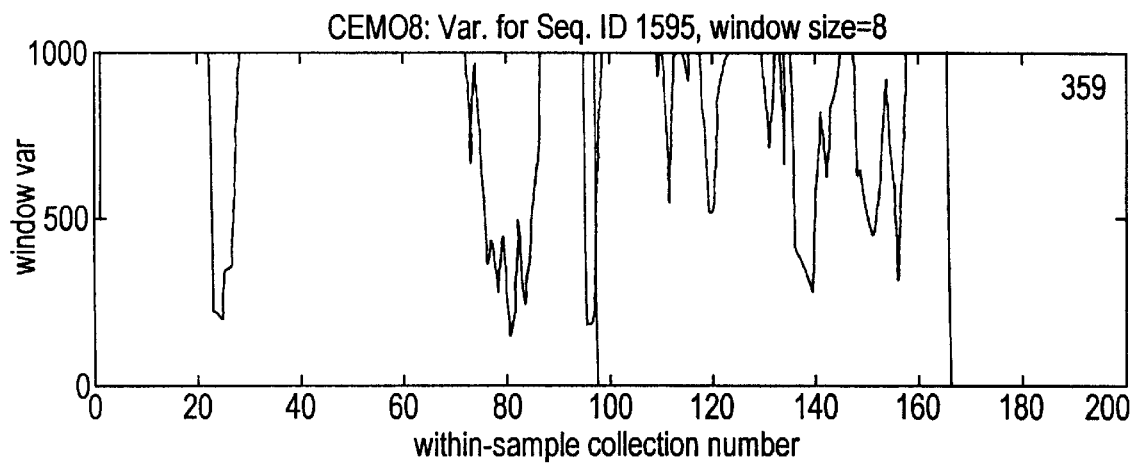
Figure 3A:
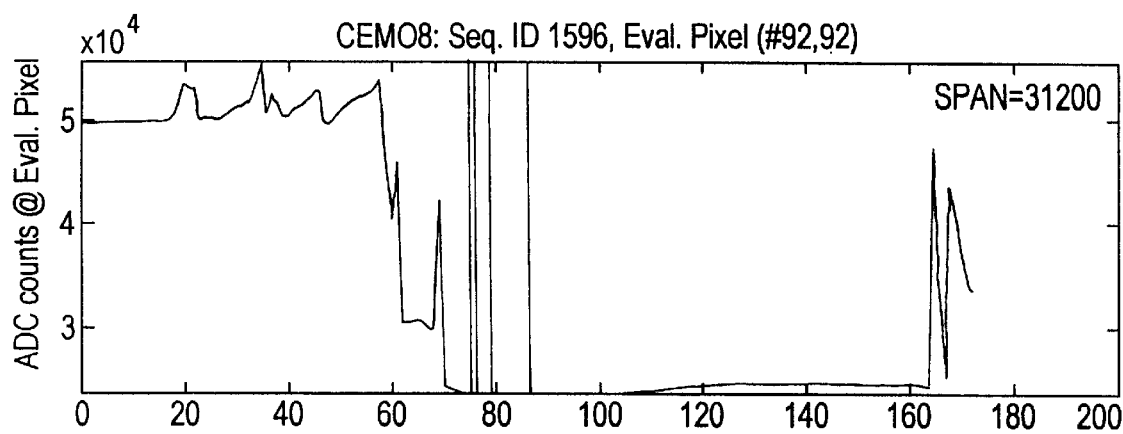
FIGS. 3A–3C illustrate signal readings for test sample 1596 where.
Figure 3B:
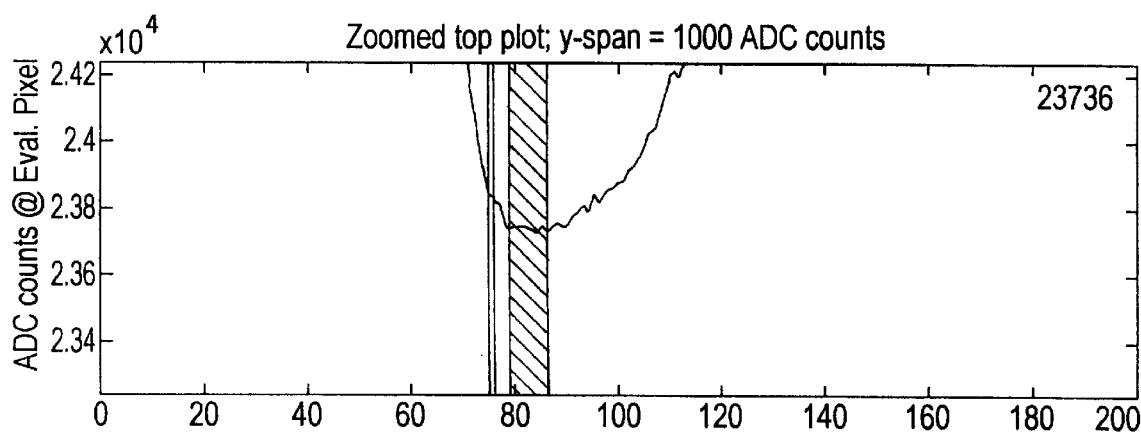
Figure 3C:
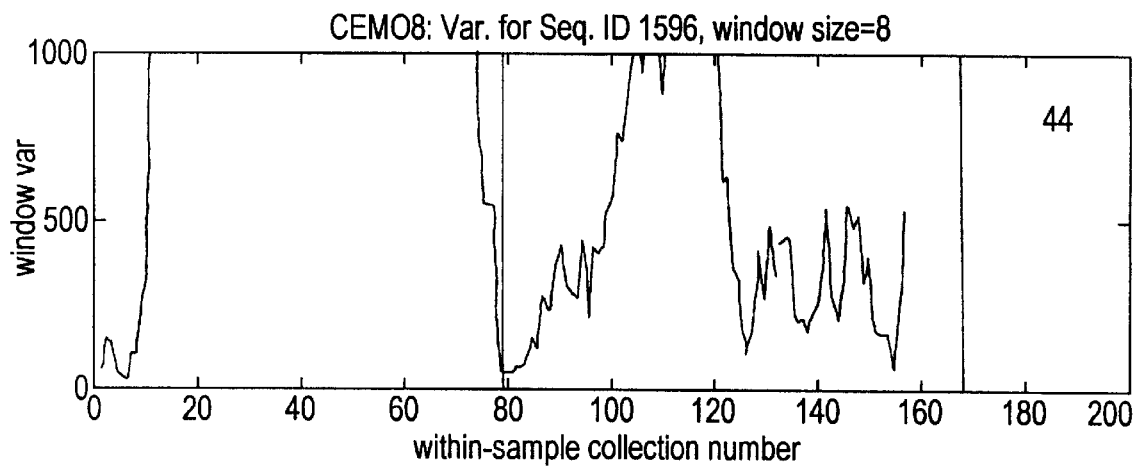
Figure 4A:
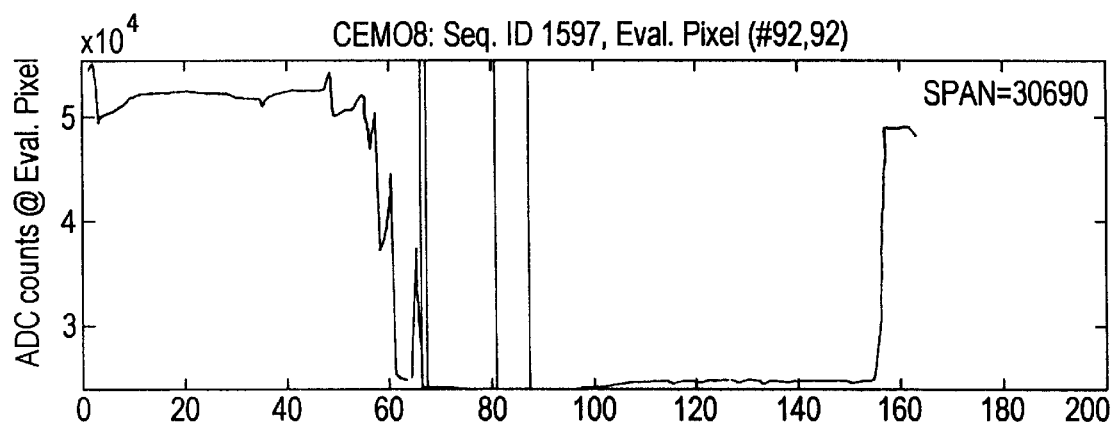
FIGS. 4A–4C illustrate signal readings for test sample 1597 where.
Figure 4B:
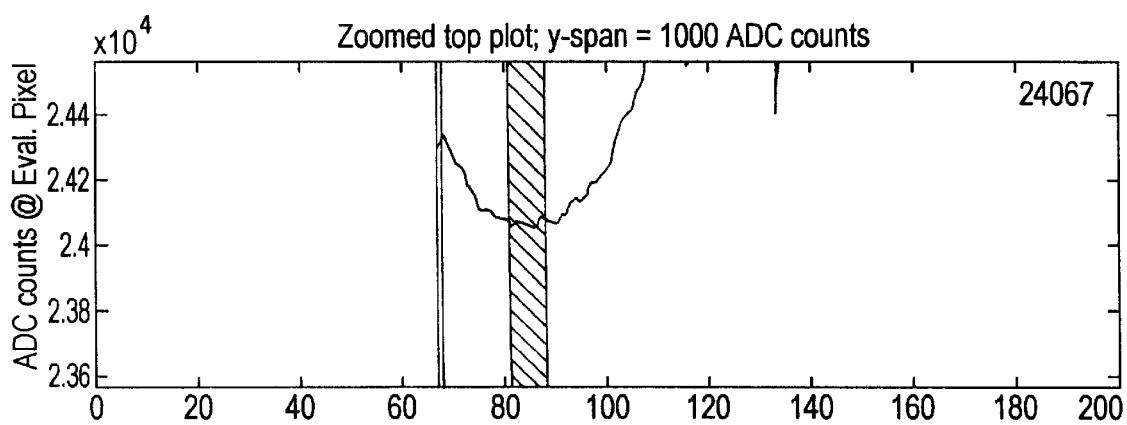
Figure 4C:
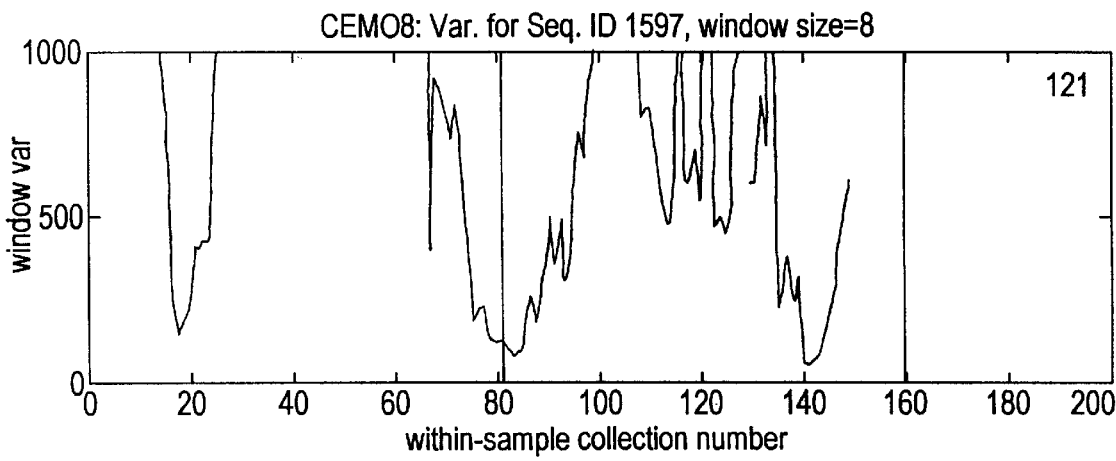

Referring to the arrows on FIG. 2B (immediately before and after the selected window) indicate inhomogeneities present in the test sample as reflected by signal measurement variation. Referring to the arrows on FIG. 6B (after the selected window) indicate dilution or microbubble effects present in the test sample. FIG. 8B shows a very good sample run, relatively free of inhomogeneities.

Table I provides the resultant hemoglobin derivative or fraction concentrations for test samples 1595–1602, the variance of each test sample and statistical analysis of the set of data. An analysis of each of FIGS. 3–10 shows that the signal measurements for each test sample were variable, but with proper window selection by the algorithm provided acceptable test results were obtained.

TABLE I

| Smpl ID | tHb | HHb | O2Hb | COHb | MetHb | fit coef | var |
|---|---|---|---|---|---|---|---|
| 001595 | 4.42 | −2.25 | −0.54 | 103.24 | −0.46 | 7.407e−009 | 359 |
| 001596 | 4.47 | −2.07 | −0.48 | 102.85 | −0.30 | 1.400e−008 | 44 |
| 001597 | 4.41 | −2.05 | −0.45 | 102.77 | −0.27 | 6.950e−009 | 121 |
| 001598 | 4.44 | −1.95 | −0.42 | 102.76 | −0.39 | 2.642e−009 | 122 |
| 001599 | 4.38 | −2.04 | −0.37 | 102.97 | −0.56 | 6.558e−009 | 160 |
| 001600 | 4.43 | −1.99 | −0.47 | 102.74 | −0.28 | 4.983e−009 | 318 |
| 001601 | 4.39 | −1.86 | −0.28 | 102.43 | −0.28 | 1.881e−009 | 63 |
| 001602 | 4.32 | −1.86 | −0.24 | 102.45 | −0.35 | 3.366e−009 | 135 |
| All Means: | 4.41 | −2.01 | −0.41 | 102.78 | −0.36 | | |
| All STDs: | 0.05 | 0.13 | 0.10 | 0.26 | 0.10 | | |

7. Examples 11–20

A blood sample from a health voluntary donor was divided into nine (9) test samples 2049–2057. Each sample was introduced into a prototype co-oximeter (800 series, Ciba Corning Diagnostics Corp.) for measurement of hemoglobin derivatives or fractions. The test sample is hemolyzed prior to entering a fluid flow cell for signal measurements (transmittance). A lead blank sample, 2048, consisting of an optically clear fluid was also analyzed. The signal measurements provided by the lead blank sample 2048 are utilized in the determination of test sample transmittance.

Measurement signals for each test sample and blank were made at a series of times, every 0.1 sec. for 10 sec. for a total of 100 measurements or 100 time ticks. The measurements were divided into windows or segments of 8 points or 8 time ticks. The criteria for window size is based on the collection of signals which avoid inhomogeneities in the test sample and the flow rate of the sample past the detector or the portion of measurable sample or passage through the optical flow cell. Signal measurements for each test sample and blank are provided in FIGS. 12–21 illustrating absorption spectra for the test samples. The window chosen by algorithm for the sample or blank is shown in the shaded area of each respective figure. The mean value of the data provided in the window was utilized to calculate the concentration of hemoglobin derivatives or fractions.

Referring to the arrows on FIG. 12B (immediately before and after the selected window) indicate inhomogeneities present in the test sample as reflected by signal measurement variation. Referring to the arrows on FIG. 14B (after the selected window) indicate dilution or microbubble effects present in the test sample.

Table II provides the resultant hemoglobin derivative or fraction concentrations for test samples 2049–2057, the variance of each test sample and statistical analysis of the set of data. An analysis of each of FIGS. 12–21 shows that the signal measurements for each test sample were variable, but with proper window selection by the algorithm provided acceptable test results were obtained with the exception of sample 2056.

In regard to the test sample 2056, it is noted that the signal variance, 872, was large in comparison to the signal variation of test samples 2049–2055 and 2057. This variation would cause the sample to be rejected according to the thresholds set for the algorithm.

TABLE II

| Smpl ID | tHb | HHb | O2Hb | COHb | MetHb | fit coef | var |
|---|---|---|---|---|---|---|---|
| 002049 | 17.97 | −1.00 | −0.49 | 101.55 | −0.06 | 4.178e−009 | 435 |
| 002050 | 18.09 | −1.11 | −0.64 | 101.73 | 0.02 | 6.739e−009 | 201 |
| 002051 | 18.03 | −0.94 | −0.31 | 101.21 | 0.03 | 4.891e−009 | 79 |
| 002052 | 17.94 | −1.03 | −0.31 | 101.34 | −0.01 | 2.950e−009 | 173 |
| 002053 | 18.07 | −1.07 | −0.45 | 101.42 | 0.11 | 4.845e−009 | 157 |
| 002054 | 17.50 | −1.12 | −0.15 | 101.31 | −0.04 | 4.841e−009 | 379 |
| 002055 | 18.16 | −0.99 | −0.25 | 101.18 | 0.06 | 4.394e−009 | 233 |
| 002056 | 14.40 | −1.04 | −0.20 | 101.02 | −0.18 | 6.080e−009 | 872 |
| 002057 | 17.97 | −1.07 | −0.21 | 101.22 | 0.07 | 3.559e−009 | 198 |
| All Means: | 17.5710 | −1.0423 | −0.2884 | 101.3307 | 0.0000 | | |
| All STDs: | 1.2028 | 0.0598 | 0.2386 | 0.2129 | 0.0861 | | |

TABLE II-continued

| Smpl ID | tHb | HHb | O2Hb | COHb | MetHb | fit coef | var |
|---|---|---|---|---|---|---|---|
| Means: | 17.9538 | −1.0413 | −0.3513 | 101.3700 | 0.0225 | | |
| STDs: | 0.2049 | 0.0624 | 0.1632 | 0.1902 | 0.0575 | | |
| (Without Sample #2056) | | | | | | | |

It should be understood that various modifications to the teaching may be made without departing from the scope of the appended claims.

We claim:

1. A method for spectroscopic analysis of fluid test samples comprising:
    (a) providing a test sample for spectroscopic analysis to an optical cell;
    (b) performing a plurality of signal measurements on said test sample;
    (c) selecting from said signal measurements one or more sets of measurements having both low variability relative to the range of variation of the signal measurements or a defined threshold, and either signal level maxima or signal level minima; and
    (d) analyzing the test sample utilizing said one or more selected set of signal measurements.

2. The method, as provided in claim 1, wherein said signal measurements are selected by performing a temporal scan or a spatial scan of the test sample.

3. The method, as provided in claim 1, wherein a single set of signal measurements or window is selected to analyze the test sample.

4. The method, as provided in claim 1, wherein said signal measurements include either transmittance, absorbance, or reflectance measurements.

5. The method, as provided in claim 3, wherein the mean value of said set of signal measurements is utilized to analyze the test sample.

6. The method, as provided in claim 1, wherein said signal measurements are performed serially over consecutive time intervals.

7. The method, as provided in claim 1, wherein said plurality of signal measurements are performed in a period of time less than or equal to ten seconds.

8. The method, as provided in claim 6, wherein each signal measurement is performed in less than or equal to 0.1 second.

9. The method, as provided in claim 1, wherein said set of measurements is greater than or equal to four signal measurements.

10. The method, as provided in claim 1, wherein said set of signal measurements is selected by use of the algorithm:

$$\text{Variability} = \sum_{i=2}^{n} abs(\text{data}_i - \text{data}_1)$$

11. The method, as provided in claim 1, wherein said signal measurements are performed while the test sample is flowing through said optical cell.

12. The method, as provided in claim 1, wherein said test sample consists of blood.

13. The method, as provided in claim 12, wherein said blood is hemolyzed.

14. The method, as provided in claim 1, wherein said signal measurements are performed while the test sample is stationery in said optical cell.

15. A method of performing optical flow cell transmittance measurements of inhomogeneous blood samples comprising:
    (a) providing a fluid test sample to an optical cell;
    (b) performing a plurality of transmittance measurements on said test sample;
    (c) selecting from said transmittance measurements one or more sets of transmittance measurements having both low variability relative to the range or group of signal measurements or to defined threshold; and either transmittance maxima; or transmittance minima signal levels; and
    (d) utilizing selected set of transmittance measurements to analyze said test sample.

16. The method of claim 15, wherein the average value of the transmittance measurements of one selected set is utilized to analyze said sample.

17. The method, as provided in claim 15, wherein said signal measurements are performed while the test sample is flowing through said optical cell.

18. The method, as provided in claim 15, wherein said signal measurements are selected by either using a temporal scan or a spatial scan of the test sample.

19. The method, as provided in claim 15, wherein said signal measurements are performed while the test sample is stationery in said optical cell.

20. In a method of performing a series of spectral signal measurements of a test sample, wherein the improvement comprises: selecting a set of spectral measurements having both low variability, relative to the range or group of sample measurements or to a defined threshold, and one of high or low spectral signal levels, wherein said set of measurements is made at a single spectral region and is utilized for analyzing said test sample.

21. The method of claim 20, wherein the selection of sets of high or low spectral measurements is determined to avoid the effect of an inhomogeneity in the test sample to the spectral signals.

22. The method of claim 20, wherein the mean value of said signal measurements of a single set of spectral measurements is utilized to analyze said sample.

23. The method of claim 20, wherein said method further comprises: flowing said test sample through an optical flow cell, and wherein sample measurements are taken while the test sample flows through optical flow cell.

24. The method of claim 20, wherein the variability of said measurements is determined by the formula $$\text{Variability} = \sum_{i=2}^{n} abs(\text{data}_i - \text{data}_1)$$

25. The method, as provided in claim 20, wherein said signal measurements are selected by either using a temporal scan or a spatial scan of the test sample.

26. In a method of performing a plurality of spectral measurements on a test sample, wherein the improvement comprises: selecting a set of signal measurements having low variability relative to the range or group of signal measurements or to a defined threshold; and utilizing said selected set of measurements to analyze said test sample.

27. In a method as recited in claim 26, wherein said set of signal measurements also consists of either high or low signal levels of spectral measurement to avoid the effect of inhomogeneities in said test sample.

28. A method for multiple wavelength spectroscopic analysis of hemoglobin fractions, wherein the improvement comprises: selecting a wavelength for an absorbance maxima of a blood sample and utilizing the results of a plurality of signal measurements at said wavelength to select a set of signal measurements from which data is provided at other wavelengths for use in determining the concentration of said hemoglobin fractions, wherein the selected set of signal measurements exhibits low variability to inhomogeneities in the blood sample.

* * * * *